(12) United States Patent
Park et al.

(10) Patent No.: US 8,809,295 B2
(45) Date of Patent: Aug. 19, 2014

(54) COMPOSITION CONTAINING INHIBITORS OF THE EXPRESSION OR ACTIVITY OF SH3RF2 FOR PREVENTING OR TREATING CANCER

(75) Inventors: Kyung Chan Park, Daejeon (KR); Young Il Yeom, Daejeon (KR); Tae Woo Kim, Daejeon (KR); Zee-Yong Park, Daejeon (KR); Yun Kyung Kang, Daejeon (KR); Suk-Jin Yang, Daejeon (KR); Byung-Jung Choi, Daejeon (KR); Dong Chul Lee, Daejeon (KR); Hyun Ahm Shon, Daejeon (KR); Hyang-Sook Yoo, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/574,055

(22) PCT Filed: Jan. 7, 2011

(86) PCT No.: PCT/KR2011/000108
§ 371 (c)(1),
(2), (4) Date: Jul. 19, 2012

(87) PCT Pub. No.: WO2011/090283
PCT Pub. Date: Jul. 28, 2011

(65) Prior Publication Data
US 2012/0321635 A1    Dec. 20, 2012

(30) Foreign Application Priority Data

Jan. 19, 2010 (KR) .................. 10-2010-0004770

(51) Int. Cl.
| | | |
|---|---|---|
| *C12N 15/11* | (2006.01) | |
| *C12N 15/113* | (2010.01) | |
| *A61K 31/7105* | (2006.01) | |
| *A61K 31/7088* | (2006.01) | |

(52) U.S. Cl.
CPC ......... *A61K 31/7088* (2013.01); *C12N 2310/14* (2013.01); *C12N 15/113* (2013.01); *A61K 31/7105* (2013.01)
USPC ...................................... 514/44 A

(58) Field of Classification Search
USPC ....................................... 514/44 A
See application file for complete search history.

(56) References Cited

U.S. PATENT DOCUMENTS

| | | | |
|---|---|---|---|
| 2003/0166229 A1* | 9/2003 | Shannon ...................... | 435/199 |
| 2009/0163434 A1* | 6/2009 | Bader et al. .................... | 514/44 |

FOREIGN PATENT DOCUMENTS

| | | |
|---|---|---|
| WO | WO2008/073919 A2 * | 6/2008 |
| WO | WO 2009/124090 | 10/2009 |

OTHER PUBLICATIONS

Chou et al. "Identification of Genetic Networks During Mesenchymal Stem Cell Transformation into Neurons" Chinese Journal of Physiology 2008 51(4):230-246.
Knowles et al. "Genome-Wide Changes Accompanying Knockdown of Fatty Acid Synthase in Breast Cancer" BMC Genomics 2007 8:168.
Nishiu et al. "Distinct Pattern of Gene Expression in Pyothorax-Associated Lymphoma (PAL), a Lymphoma Developing in Long-Standing Inflammation" Cancer Science 2004 95(10):828-834.
International Search Report from PCT/KR11/00108, Sep. 27, 2011, PCT.

* cited by examiner

*Primary Examiner* — Brian Whiteman
(74) *Attorney, Agent, or Firm* — Licata & Tyrrell P.C.

(57) ABSTRACT

The present invention relates to a composition comprising an inhibitor of the expression or activity of SH3 domain containing ring finger 2 (SH3RF2) for preventing or treating cancers. More specifically, since the SH3RF2 protein, of which the expression level increases in various cancer tissues, binds to PAK4, which is a cancer-associated gene, to regulate an apoptosis inhibitory function of the PAK4 protein by ubiquitination activity of SH3RF2 RING domain, cancer cells, in which the expression of SH3RF2 is inhibited, sensitively respond to the induction of apoptosis to promote apoptosis and reduce in vivo tumorigenicity, such that the inhibitor of the expression or activity of SHRF2 can be useful as a composition for preventing or treating cancers.

5 Claims, 14 Drawing Sheets

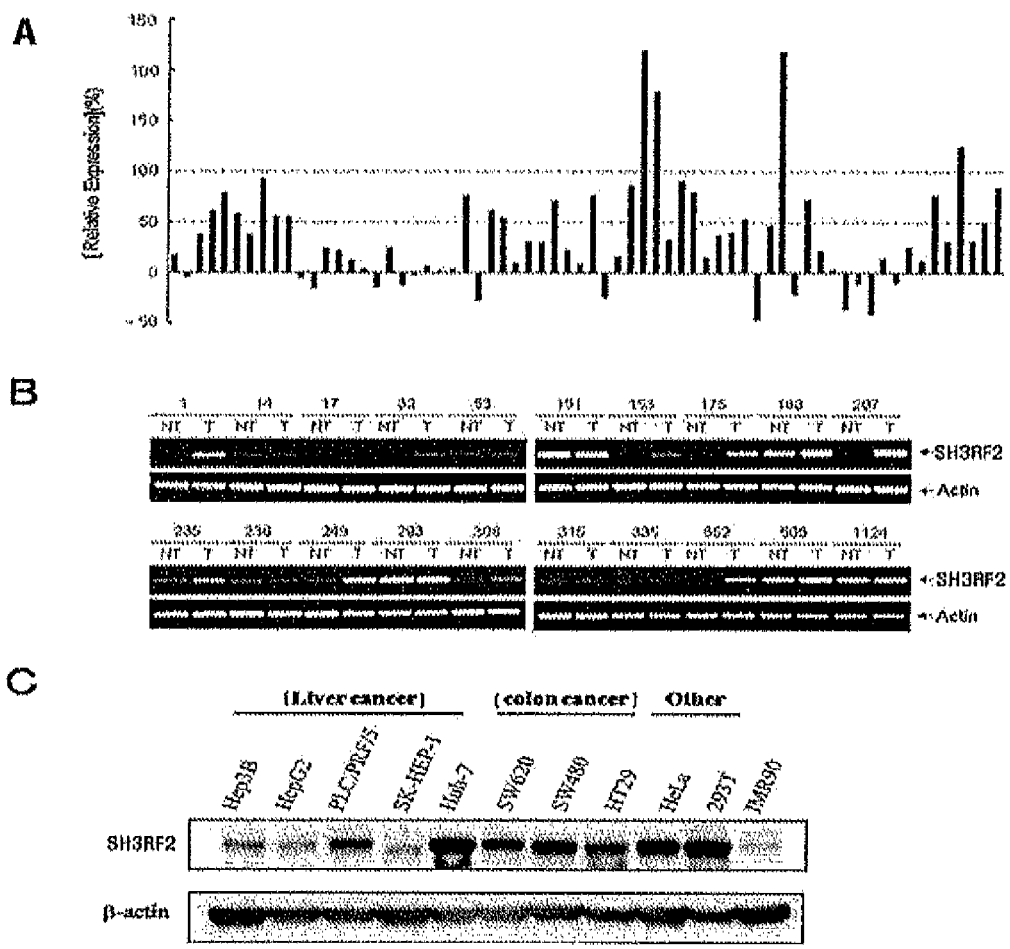

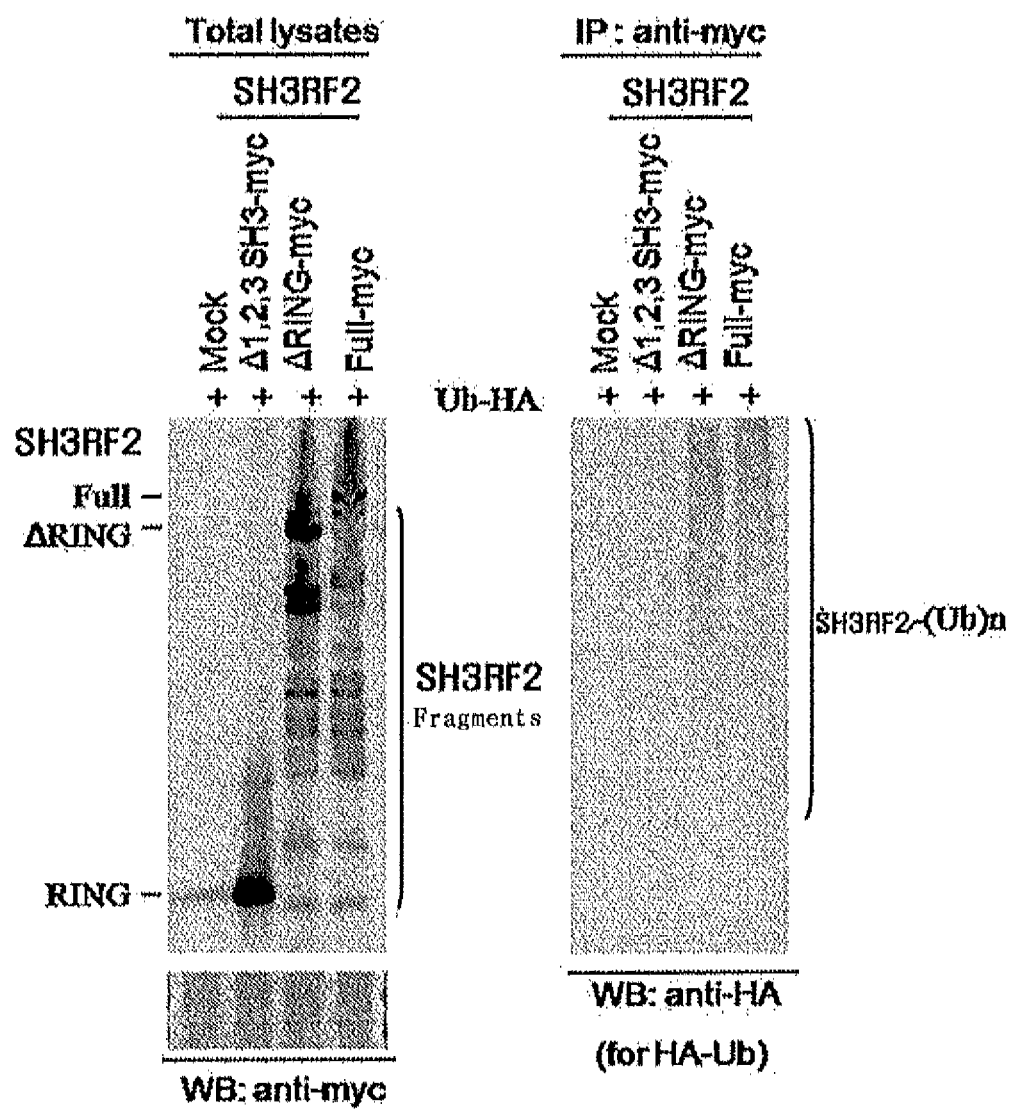

Fig. 4
A
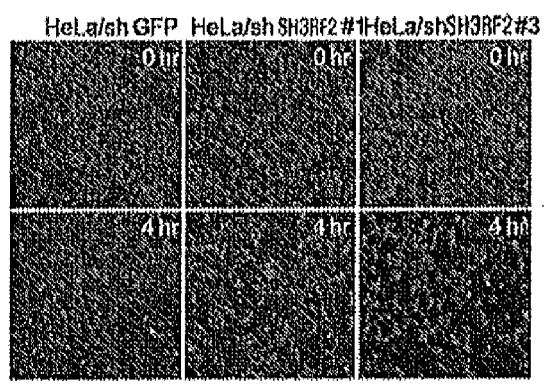
B
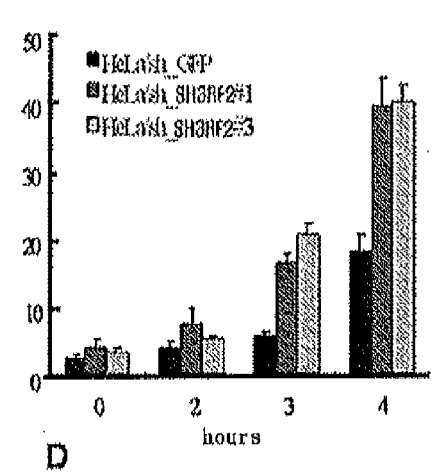
C
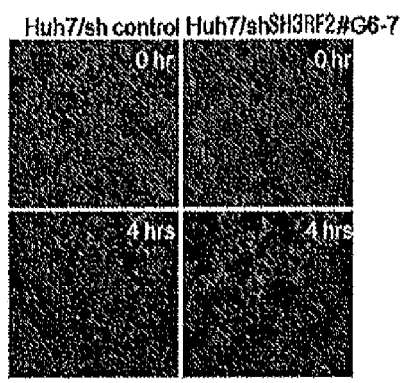
D
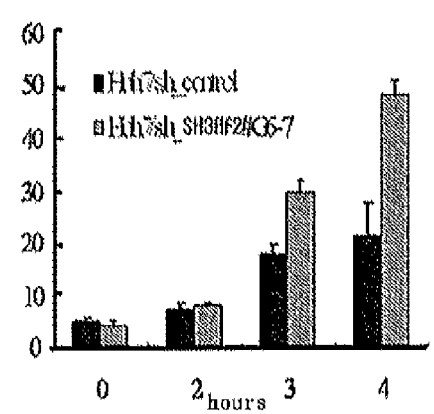

Fig. 5
A
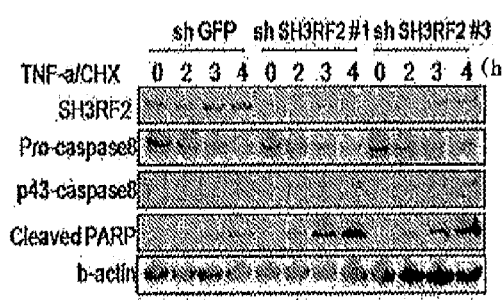
B
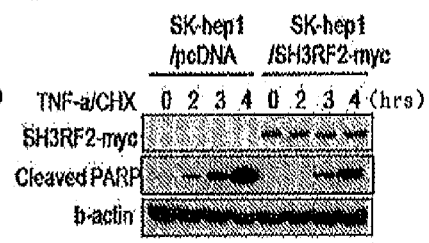
C
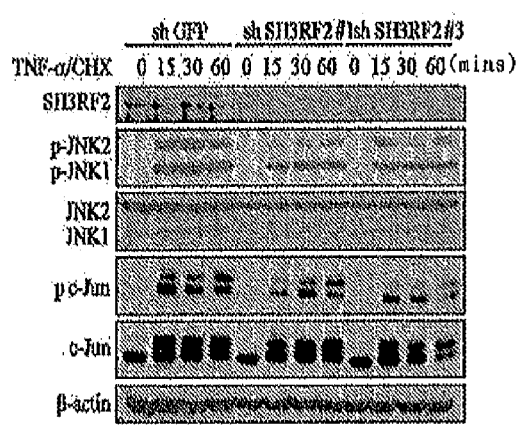
D
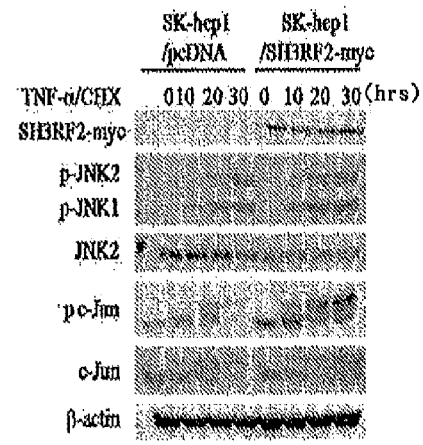

Fig. 6a
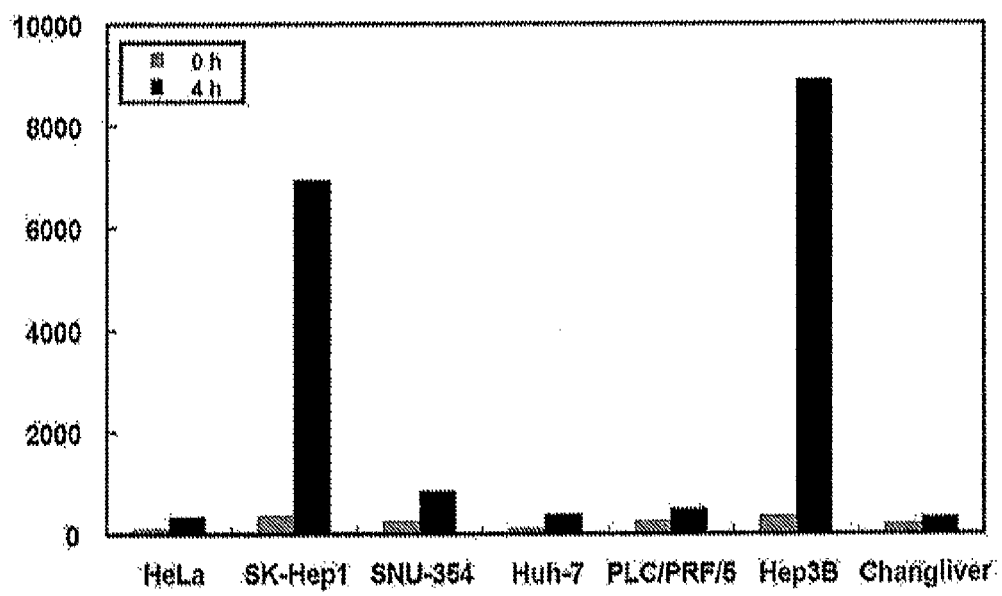
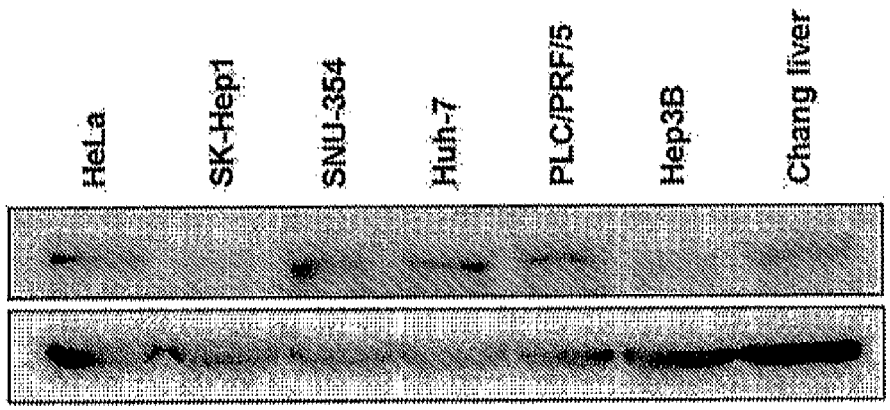

Fig. 8
A
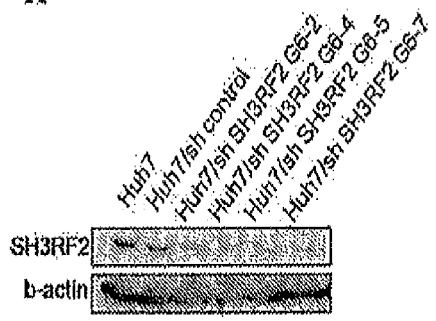
B
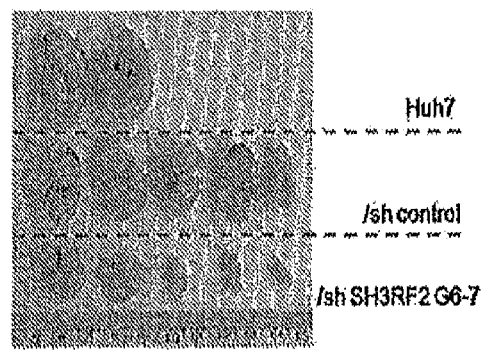
C
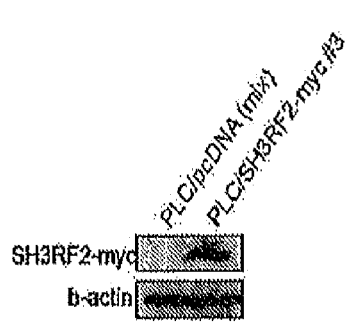
D
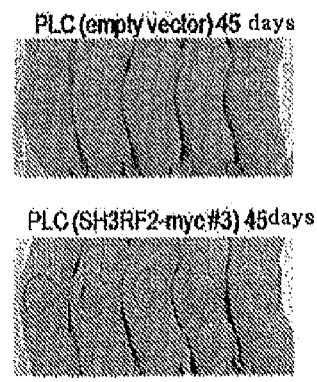

Fig. 9b

| Clinicopathologic parameter | SH3RF2 Expression | | P value |
|---|---|---|---|
| | Negative | Positive | |
| Age | | | |
|   Young(< 53) | 23 | 29 | 0.006 |
|   Elderly(> 54) | 37 | 15 | |
| Sex | | | |
|   Male | 54 | 37 | 0.370 |
|   Female | 6 | 7 | |
| Tumor size | | | |
|   Small(< or = 5) | 33 | 20 | 0.338 |
|   Large (> 5) | 27 | 24 | |
| TNM stage | | | |
|   I-II | 38 | 13 | 0.001 |
|   III-IV | 22 | 31 | |
| Edmondson grade | | | |
|   Grade 1/2 | 26 | 5 | 0.000 |
|   Grade 3/4 | 34 | 39 | |
| Portal vein thrombi | | | |
|   Absent | 31 | 11 | 0.011 |
|   Microscopic | 16 | 17 | |
|   Gross | 13 | 16 | |
| Growth pattern | | | |
|   Expansile | 47 | 30 | 0.246 |
|   Infiltrative | 13 | 14 | |
| Intrahepatic metastasis | | | |
|   Absent | 43 | 23 | 0.043 |
|   Present | 17 | 21 | |
| Lymph node metastasis | | | |
|   Absent | 53 | 32 | 0.043 |
|   Present | 7 | 12 | |
| Recurrent HCC | | | |
|   Absent | 22 | 7 | 0.043 |
|   Present | 36 | 31 | |
| Serum anti-HBV | | | |
|   Negative | 20 | 7 | 0.046 |
|   Positive | 40 | 37 | |
| Serum anti-HCV | | | |
|   Negative | 51 | 43 | 0.107 |
|   Positive | 6 | 1 | |

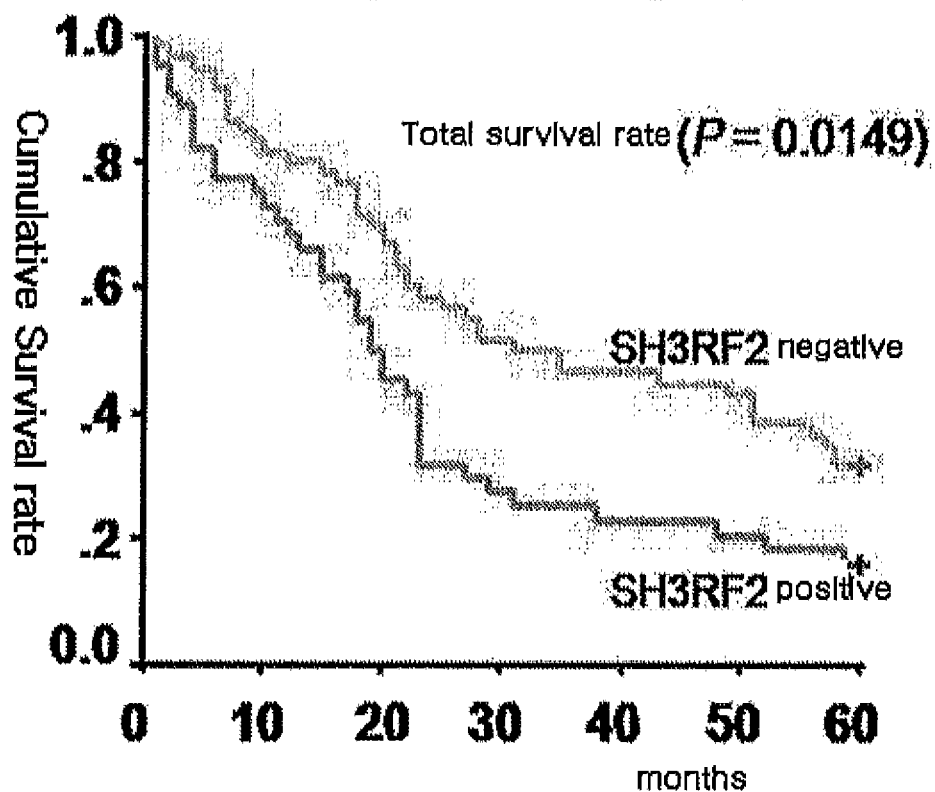

COMPOSITION CONTAINING INHIBITORS OF THE EXPRESSION OR ACTIVITY OF SH3RF2 FOR PREVENTING OR TREATING CANCER

CROSS-REFERENCES TO RELATED APPLICATION

This patent application is the National Stage of International Application No. PCT/KR2011/000108, filed Jan. 7, 2011, which claims the benefit of priority from Korean Patent Application No. 10-2010-0004770 filed on Jan. 19, 2010, the content of each of which are incorporated herein by reference in their entirety.

BACKGROUND OF THE INVENTION

1. Field of the Invention

The present invention relates to a composition for preventing or treating cancers.

2. Description of the Related Art

Cancer is one of the greatest diseases threatening health of mankind and occurs when cells go through a series of mutation process, proliferate in an unlimited and uncontrollable way, and become immortal. Examples of causes of cancer include environmental or external factors such as chemicals, viruses, bacteria, ionizing radiation, etc., and internal factors such as congenital genetic mutations (Klaunig & Kamendulis, *Annu Rev Pharmacol Toxicol.*, 44:239-267, 2004).

For cancers found in an early stage, there are therapeutic measures such as surgery, radiation therapy, chemotherapy, etc.; however, their side effects also become a big problem. For a terminal cancer or metastasized cancer, there is no specific therapeutic measure, and patients are given time-limited life and end their lives. Furthermore, various biochemical mechanisms related to cancer have been identified and the consequential therapeutic agents have been developed, however, fundamental methods for treating cancers have not yet been suggested. For this reason, efforts have been made to identify various in vivo molecules related to cancer and develop drugs which target them, and efforts have also been attempted to improve cancer-therapeutic effects by combining some of those drugs. Therefore, it is very important to endeavor to discover additional cancer-related target molecules.

SH3 domain containing ring finger 2 (SH3RF2) gene is expressed in tissues such as testis, brain, rectum, medulla, heart, lung, liver or spleen, etc., and this protein consists of 729 amino acids and includes src homology-3, SH3, zinc finger, RING-type (Pfam) and prenylation domains. The N-terminal RING domain thereof is assumed to have ubiquitin ligase activity, and this protein has three SH3 domains which bind to other proteins. SH2RF2 protein is present in various cell organelles such as mitochondria or nucleus, and regarded to perform molecular functions such as ligase activity, metal ion binding, protein binding or zinc-ion binding. However, the function of SH3RF2 has not yet been determined.

Thus, the present inventors have tried to discover new cancer-related target molecules and establish them as anticancer substances, consequently identified that the expression of SH3RF2 increases in various human tumor tissues, and SH3RF2 binds to oncogenic p21 activated kinase 4 (PAK4) to regulate an apoptosis-inhibitory function of PAK4 protein through the ubiquitination activity of SH3RF2, and inhibition of SH3RF2 expression can inhibit cancer growth, and determined that SH3RF2 inhibitors can be used as anticancer drugs or anticancer adjuvants, thereby leading to completion of the present invention.

SUMMARY OF THE INVENTION

One object of the present invention is to provide a pharmaceutical composition for preventing or treating cancers or an anticancer adjuvant, the pharmaceutical composition or the anticancer adjuvant comprising an inhibitor of the expression or activity of SH3RF2.

Another object of the present invention is to provide a method for screening an anticancer drug or anticancer adjuvant, or monitoring and diagnosing cancers, the method using the level of expression or activity of SH3RF2.

In order to achieve the objects, the present invention provides a pharmaceutical composition for preventing or treating cancers, comprising an inhibitor of the expression or activity of SH3RF2 protein.

The present invention also provides an anticancer adjuvant comprising an inhibitor of the expression or activity of SH3RF2 protein.

Furthermore, the present invention provides a method for screening candidate substances for an anticancer drug or anticancer adjuvant, the method comprising:

(1) treating an SH3RF2 protein-expressing cell line with a test substance;

(2) measuring the level of expression or activity of SH3RF2 protein of the cell line; and (3) selecting the test substance which has the decreased level of expression or activity of SH3RF2 protein, compared to a control which was not treated with the test substance.

The present invention also provides a method for screening candidate substances for an anticancer drug or anticancer adjuvant, the method comprising:

(1) bring SH3RF2 protein into contact with PAK4 protein under the presence of a test substance;

(2) measuring the level of binding between SH3RF2 protein and PAK4 protein; and (3) selecting the test substance which has the decreased level of binding between SH3RF2 protein and PAK4 protein, compared to a control which was not treated with the test substance.

Furthermore, the present invention provides a method for screening candidate substances for an anticancer drug or anticancer adjuvant, the method comprising:

(1) treating an SH3RF2 protein and ubiquitin protein-expressing cell line with a test substance;

(2) measuring the level of ubiquitination activity of SH3RF2 protein of the cell line; and (3) selecting the test substance which has the decreased level of ubiquitination activity of SH3RF2 protein, compared to a control which was not treated with the test substance.

The present invention also provides a method for diagnosing cancers, identifying therapeutic results, or assessing prognosis, the method comprising measuring SH3RF2 expression level in cancer cells, using any one or more of antibodies reactive with SH3RF2 protein or nucleic acids complementary to SH3RF2 gene.

Furthermore, the present invention provides a kit for diagnosing cancers, comprising any one or more of antibodies reactive with SH3RF2 protein or nucleic acids complementary to SH3RF2 gene.

The present invention also provides a method for preventing cancers, comprising administering a pharmaceutical composition which comprises a pharmaceutically effective amount of an inhibitor of the expression or activity of SH3RF2 protein as an active ingredient to an individual.

Furthermore, the present invention provides a method for treating cancers, comprising administering a pharmaceutical composition which comprises a pharmaceutically effective amount of an inhibitor of the expression or activity of SH3RF2 protein as an active ingredient to an individual having cancer.

The present invention also provides a method for promoting apoptosis, comprising treating hyperplastic cells with an inhibitor of the expression or activity of SH3RF2 protein.

Furthermore, the present invention provides a use for utilizing an inhibitor of the expression or activity of SH3RF2 protein for preparation of a pharmaceutical composition for preventing or treating cancers.

The present invention also provides a use for utilizing an inhibitor of the expression or activity of SH3RF2 protein for preparation of an anticancer adjuvant.

Furthermore, the present invention provides a use for utilizing an antibody reactive with SH3RF2 protein or a nucleic acid complementary to SH3RF2 gene for preparation of a kit for diagnosing cancers.

Inhibitors of the expression or activity of SH3RF2 of the present invention inhibit the expression or activity of SH3RF2, of which the expression level increases in various tumor tissues and there is a significant relationship between this increase in the expression and the growth and metastasis of cancers, and which binds to oncogenic PAK4 to regulate an apoptosis-inhibitory function of PAK4 protein through ubiquitination activity, and thus can inhibit growth and metastasis of cancers through the inhibition of SH3RF2. Therefore, inhibitors of the expression or activity of SH3RF2 of the present invention can be effectively used as an active ingredient of anticancer drugs or anticancer adjuvants, and can be effectively used for screening candidate substances for an anticancer drug or anticancer adjuvant, or diagnosing cancers.

BRIEF DESCRIPTION OF THE DRAWINGS

The above and other objects, features and other advantages of the present invention will be more clearly understood from the following detailed description taken in conjunction with the accompanying drawings, in which:

FIG. 1 is diagrams illustrating DNA chip analyses of colon cancer tissues:
A: SH3RF2 mRNA expressions in tumor tissues or normal tissues of 66 cases of colon cancer tissues;
B: SH3RF2 mRNA expressions in tumor tissues or normal tissues of 20 cases of colon cancer tissues randomly selected from 66 cases; and
C: SH3RF2 protein expressions in various cancer cell lines.

FIG. 2 is diagrams illustrating the ubiquitination activity of SH3RF2:
FIG. 2b: Ubiquitin ligase activity of SH3RF2.

FIG. 4 is diagrams illustrating the effect of suppression of SH3RF2 expression on the apoptosis induction:
A: DNA condensation through Hoechst staining in HeLa cell line;
B: Quantification of percentage of the number of Hoechst-stained cells in HeLa cell line;
C: DNA condensation through Hoechst staining in Huh7 liver cancer cell line; and
D: Quantification of percentage of the number of Hoechst-stained cells in Huh7 liver cancer cell line.

FIG. 5 is diagrams illustrating changes in the downstream signals of TNF-α in accordance with changes in the expression amount of SH3RF2:
A: Expression of apoptotic marker proteins in cell line which inhibited SH3RF2 expression;
B: Expression of apoptotic marker proteins in cell line which overexpressed SH3RF2;
C: Expression of active JNK and AP1 transcription factor in cell line which inhibited SH3RF2 expression; and
D: Expression of active JNK and AP1 transcription factor in SH3RF2 overexpressed cell line.

FIG. 6 is diagrams illustrating the effect of the expression level of SH3RF2 on the apoptosis by TNF-α/CHX:
FIG. 6a: The level of response (A) and the level of SH3RF2 protein expression amount (B) from apoptosis by TNF-α treatment of different kinds of cancer cell lines.

FIG. 8 is diagrams illustrating in vivo tumorigenicity of SH3RF2 expression-inhibited or -overexpressed cell lines using a mouse model:
A: Determination of SH3RF2 expression amount in liver cancer cell line which inhibited SH3RF2 expression;
B: Tumorigenicity of liver cancer cell line which inhibited expression of SH3RF2 in a nude mouse;
C: Determination of SH3RF2 expression amount in SH3RF2-overexpressed liver cancer cell line; and
D: Tumorigenicity of SH3RF2-overexpressed liver cancer cell line in a nude mouse.

FIG. 9 is diagrams illustrating the correlation between liver cancer patients and SH3RF2 expression:
FIG. 9b: The correlation between SH3RF2 expression and clinical data of liver cancer patients;
and
FIG. 9c: The correlation between SH3RF2 expression and viability of liver cancer patients.

DESCRIPTION OF THE PREFERRED EMBODIMENTS

Hereinafter, the present invention will be described in greater detail.

The present invention provides a pharmaceutical composition for preventing or treating cancers, comprising an inhibitor of the expression or activity of SH3RF2 protein.

The SH3RF2 protein may comprise, but not limited to, an amino acid sequence of SEQ ID NO:1.

The SH3RF2 protein expression inhibitor may be, but not limited to, any one selected from the group consisting of antisense nucleotides, small interfering RNAs (short interfering RNAs), and short hairpin RNAs, which bind complementarily to mRNA of SH3RF2 gene having nucleotide sequence of SEQ ID NO:2.

The SH3RF2 protein activity inhibitor may be, but not limited to, any one selected from the group consisting of compounds, peptides, peptide mimetics, aptamers, and antibodies, which bind complementarily to SH3RF2 protein.

The cancer may be any one selected from the group consisting of liver cancer, colon cancer, cervical cancer, renal cancer, stomach cancer, prostate cancer, breast cancer, brain tumor, lung cancer, uterine cancer, colorectal cancer, bladder cancer, hematologic malignancy, and pancreatic cancer, and more preferably, it may be, but not limited to, liver cancer, colon cancer, cervical cancer, or renal cancer, and include any cancer caused by excessive expression or activity of SH3RF2.

In order to determine the expression amount of SH3RF2 in various cancer (liver cancer, colon cancer, cervical cancer, or renal cancer) tissues, the present inventors examined the expression amount of SH3RF2 gene or protein through DNA chip, RT-PCR, or Western blot analyses. Consequently, SH3RF2 was found to be remarkably highly expressed in various cancer cell lines compared to normal cell line (FIG. 1).

Figure 2A:
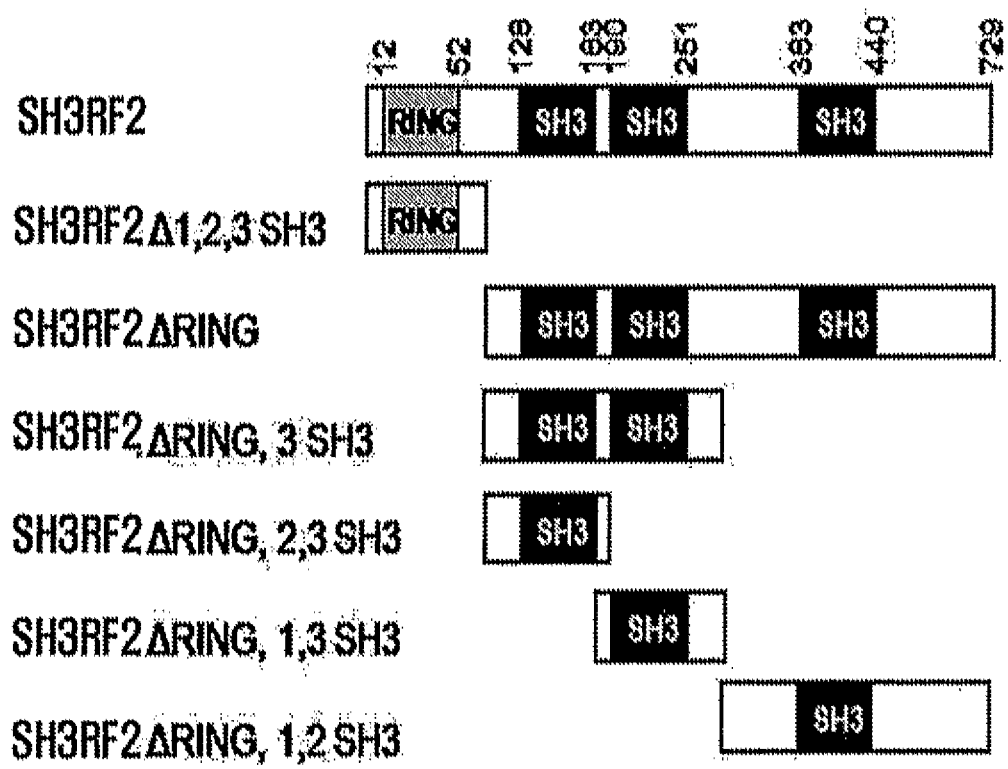
FIG. 2a: Diagrams of SH3RF2 gene domains and their mutants.

In order to determine the ubiquitination activity of SH3RF2, the present inventors prepared mutants of the RING domain being assumed to have the ubiquitin ligase activity or three SH3 domains involving protein binding (FIG. 2a), and co-transplanted them with ubiquitin protein expression vectors and carried out Western blotting to examine the ubiquitination activity. Consequently, a high molecular weight, ubiquitinated SH3RF2 was found to be in the full-length SH3RF2-transplanted cells, and SH3RF2 was found to be ubiquitinated also in cells transplanted with a mutant having no RING domain. It can be assumed that this was the ubiquitination by the existing SH3RF2 or other SH3RF2-specific E3 ligases present in cells. However, ubiquitination was not found, or it was found to be very weak, in cells transplanted with only RING domain, and it is assumed because there was no or little site for ubiquitination in short N-terminal RING domain (FIG. 2b). Furthermore, the full-length SH3RF2 (GST-SH3RF2) having a RING domain showed E3 activity, and a RING domain-deleted SH3RF2 (GST-ΔRING) did not ubiquitinate itself. UBCH5a and UBCH13/Mms E2 enzymes used here are enzymes which allow other ubiquitin to bind to $48^{th}$ and $63^{rd}$ lysine residues of ubiquitin, respectively. Thus, this shows that SH3RF2 has both the K48-ubiquitination activity, which is the protein degradation signal, and the K63-ubiquitination activity, which involves in maintaining or amplifying signal transduction.

Figure 3:
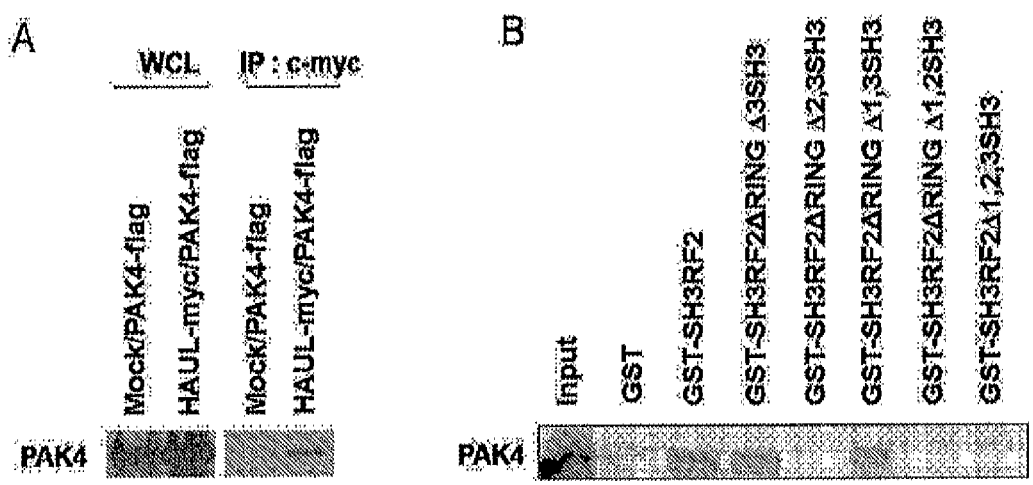
FIG. 3 is diagrams illustrating the binding between SH3RF2 protein and PAK4 protein:
A: Intracellular binding between SH3RF2 protein and PAK4 protein; and
B: SH3RF2 domain to which PAK4 binds.

In order to determine whether oncogenic p21-activated kinase 4 (PAK4) protein, which is known to be increased in cancers and involve in inhibiting apoptosis and promoting cell migration, and SH3RF2 protein bind to each other, the present inventors co-transplanted a PAK4 expression vector or an SH3RF2 expression vector and carried out immunoprecipitation (FIG. 3A) or GST-pull down assay (FIG. 3B) and Western blotting. The result showed that PAK4 and SH3RF2 proteins bind to each other within cells (FIG. 3A), and PAK4 bound to the second domain in SH3RF2 (FIG. 3B).

A previously published paper reported that PAK4 expression is involved in cancer apoptosis, and particularly, Li X. and Minden A. reported that apoptosis was promoted when cancer cells which inhibited PAK4 expression were treated with tumor necrosis factor-α (TNF-α) and cycloheximide at the same time (Li X. & Minden A., *J Biol. Chem.* 2005, 280, 41192-41200). Since the present inventors identified that SH3RF2 binds to PAK4, and PAK4 level is regulated by SH3RF2, in order to determine the effect of inhibition of SH3RF2 expression on the induction of apoptosis, TNF-α and cycloheximide were treated at one time to the cancer cell lines which inhibited SH3RF2 expression to induce apoptosis. Consequently, Results indicate that the SH3RF2 expression-inhibited cancer cell lines respond more sensitively to apoptosis than control did, so that apoptosis is promoted (FIG. 4). Whereas the expression of apoptotic markers was decreased in SH3RF2 overexpressed cancer cell lines, it was increased in cell lines which inhibited SH3RF2 expression (FIG. 5A and FIG. 5B).

Figure 6B:
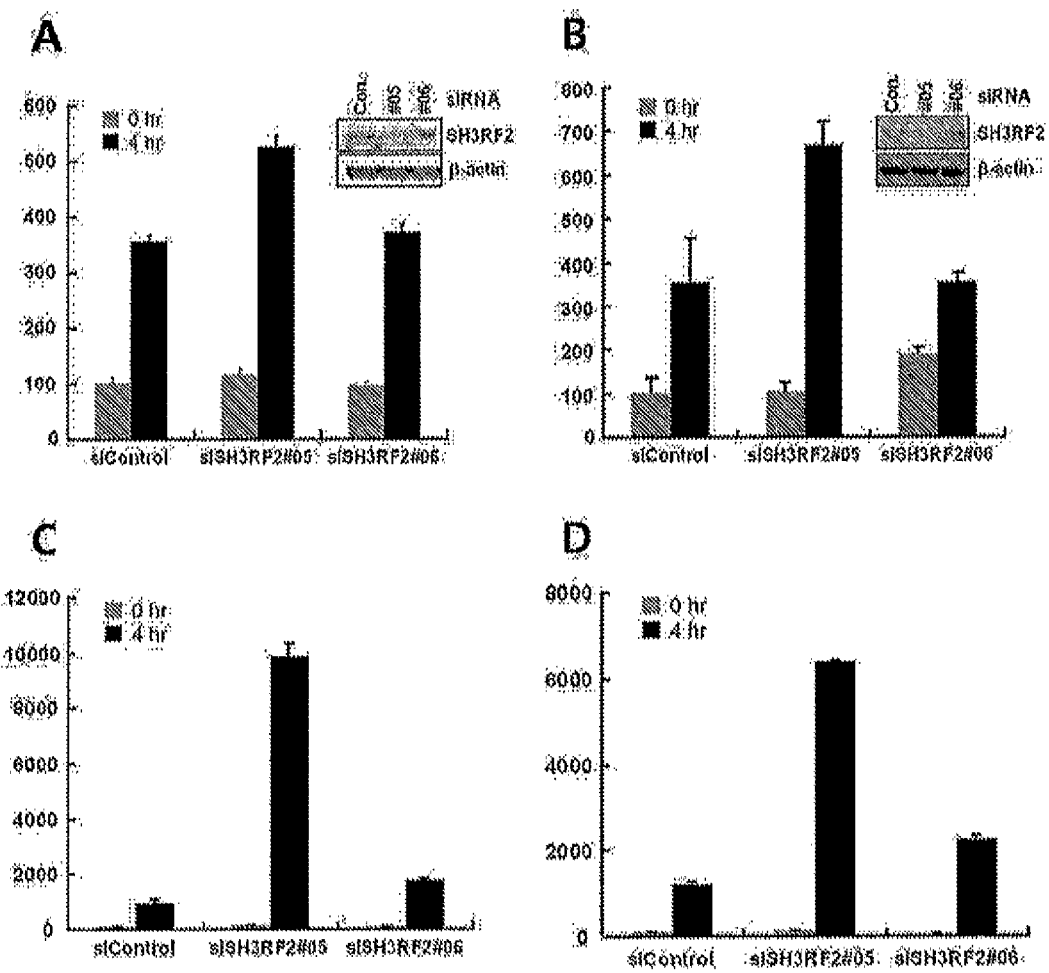
FIG. 6b: The level of apoptosis by TNF-α treatment and inhibition of SH3RF2 protein expression by siRNA, when SH3RF2 is inhibited in different kinds of cancer cell lines:
A: Liver cancer cell line Huh-7;
B: Cervical cancer cell line HeLa;
C: Liver cancer cell line SK-Hep1; and
D: Liver cancer cell line Hep3B.

There is a report that PAK4 is an upstream modulator of JNK among MAP kinase pathway, and increases signals by TNF-α (Gnesutta, N & Minden, A 2003). As a cellular reaction in response to stress, c-Jun N-terminal kinases (JNKs), one of MAPKs which are activated by MAPK kinase (MAPKK), phosphorylate c-Jun N-terminal region and regulate a transcription factor, activating protein-1 (AP-1). At this point, apoptosis is promoted by JNK1 activity, and it was reported that this mechanism of apoptosis is suppressed by JNK2 activity (Shafiq Uddin Ahmed & Jo Milner, PLoS ONE, 2009, Vol. 4, e7305). Therefore, change in JNK activity induced by change in the expression amount of SH3RF2, which is involved in the regulation of apoptosis through PAK4 activity, was examined. Results indicate that phosphorylation of JNK2 is decreased by inhibition of SH3RF2 expression, and thus, phosphorylation of the downstream c-Jun is decreased, and these indicated that the activity of AP-1, which consists of dimers of c-Jun and c-fos, can be regulated by change in SH3RF2 expression (FIG. 5C and FIG. 5D). Furthermore, in order to investigate the correlation between sensitivity to TNF-α-induced apoptosis of cancer cells and expression amount of SH3RF2 protein, apoptosis was induced by TNF-α in different kinds of cancer cells having different level of SH3RF2 expression. Results indicate that the lower the expression of SH3RF2 protein is, the higher sensitivity to TNF-α-induced apoptosis of cancer cells is (FIG. 6a and FIG. 6b). The above results indicate that when SH3RF2 expression is inhibited in cancer cell lines, apoptosis induced by TNF-α and cycloheximide treatments is promoted, and the inhibition of SH3RF2 expression increases sensitivity to TNF-α-induced apoptosis. These suggest that SH3RF2 binds directly to PAK4 protein and regulates the apoptosis-inhibitory function of PAK4 protein.

Figure 7:
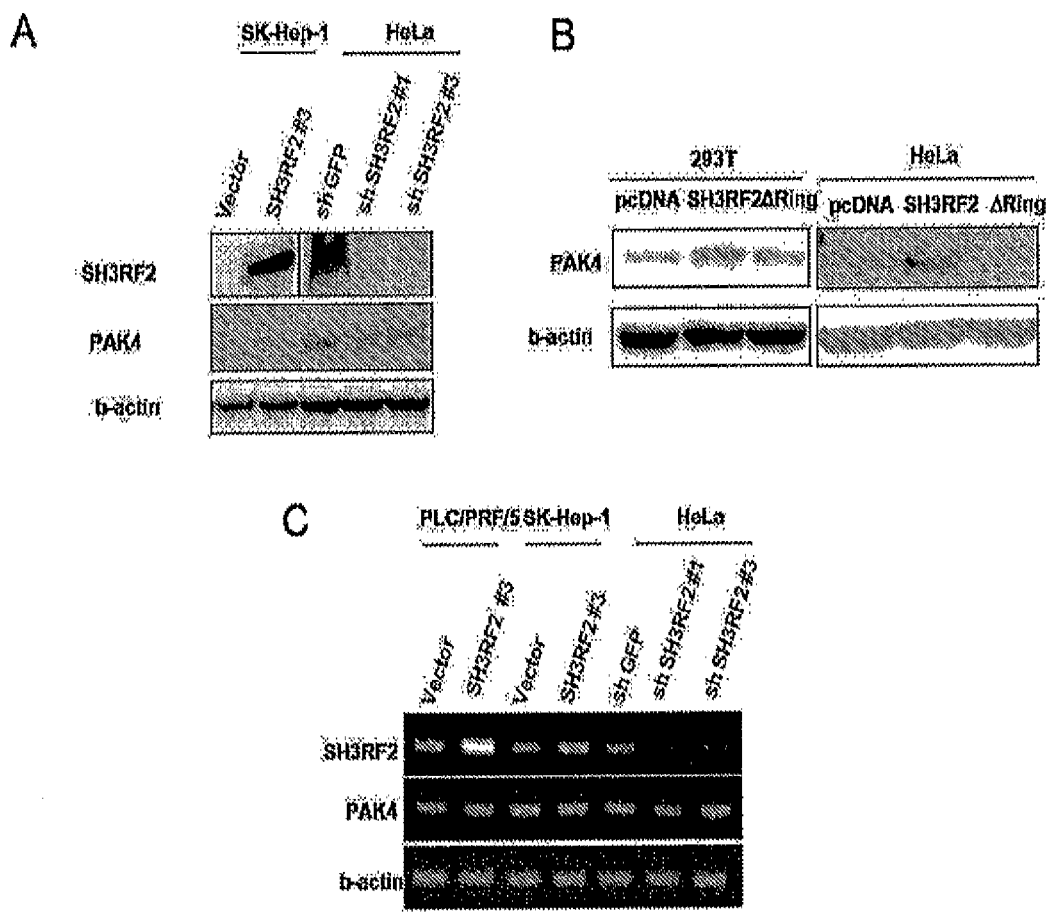
FIG. 7 is diagrams illustrating changes in the expression amount of PAK4 in accordance with changes in the expression amount of SH3RF2:
A: Expression of PAK4 protein;
B: Expression of PAK4 protein in temporarily or continuously SH3RF2-overexpressed cell line; and
C: Expression of PAK4 mRNA.

In order to determine PAK4 expression amount in accordance with changes in the expression amount of SH3RF2, the present inventors examined the expression amounts of PAK4 protein or gene in SH3RF2 expression-inhibited or—overexpressed cancer cell lines. Consequently, when SH3RF2 was expressed continuously, the expression amounts of SH3RF2 and PAK4 were proportional to each other. Since the increase in the expression amount of PAK4 was not shown in RING domain-deleted SH3RF2 overexpressed cancer cells, this indicates that the ubiquitination activity of SH3RF2 is required for the regulation of the expression of PAK4, and could suggest that inhibition of the ubiquitination activity of SH3RF2 is important as a therapeutic target for cancer or hyperplastic disease through the regulation of PAK4 (FIG. 7).

In order to determine tumorigenicity in vivo in accordance with change in SH3RF2 expression, the present inventors injected SH3RF2 expression inhibited or overexpressed cancer cell lines into a nude mouse respectively to measure tumor formation. Since when SH3RF2, which is an oncogene, was deficient, tumor formation was decreased, and when SH3RF2 was overexpressed, tumor formation was increased, results indicate that the overexpression of SH3RF2 protects cells from apoptosis and influences tumorigenicity (FIG. 8).

Figure 9A:
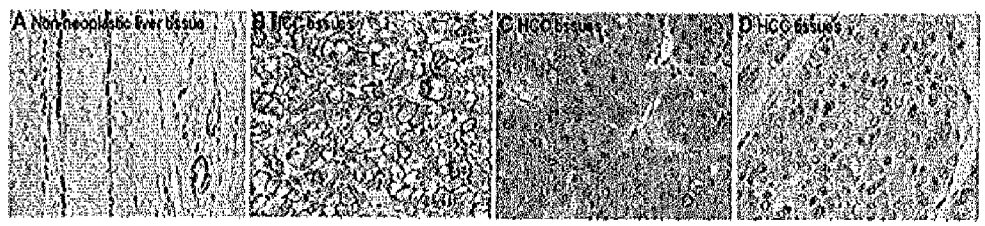
FIG. 9a: Determination of SH3RF2 protein expression in liver cancer clinical tissues using tissue microarray.

In order to determine the effect of change in the expression of SH3RF2 in cancer patients, the present inventors investigated the expressions of SH3RF2 protein in tumor tissues or normal tissues of liver cancer patients through tissue microarray (TMA). Consequently, the expression was not found in normal tissues, however, the expression was found in tumor tissues. As a result of a comparative analysis of clinical data of cancer patients and SH3RF2 expression, there is a significant relationship between SH3RF2 expression and the progression stage, type of metastasis, recurrence or survival rate of cancer (FIG. 9a, FIG. 9b, and FIG. 9c).

Therefore, since SH3RF2 binds to PAK4 protein and regulates apoptosis through the ubiquitination activity, and inhibition of SH3RF2 expression promotes apoptosis and decreases tumorigenicity, the inhibitor of the expression or activity of SH3RF2 protein can be used effectively as an active ingredient of anticancer pharmaceutical compositions.

The pharmaceutical composition may contain, in addition to the inhibitor of the expression or activity of SH3RF2 protein, one or more active ingredients having same or similar functions to the inhibitor.

The pharmaceutical composition may be administered orally or parenterally upon clinical administration. For parenteral administration, it may be administered by intraperitoneal injection, intrarectal injection, subcutaneous injection, intravenous injection, intramuscular injection, dural injection, intracerebrovascular injection, or intrathoracic injection, and may be used in general medicine forms.

The pharmaceutical composition may be used alone or in combination with surgery, radiotherapy, hormone therapy, chemotherapy, and methods using biologic response modifiers.

A daily dose of the pharmaceutically composition may be from about 0.0001 to 100 mg/kg, preferably from about 0.001 to 10 mg/kg. The daily dose may be administered once or several times per day, and may be varied depending on body weight, age, gender, health condition, diet of a patient, administration time, administration method, clearance, severity of a disease, etc.

The pharmaceutical composition of the present invention may be administered as various parenteral formulations upon actual clinical administration. Formulations may prepared by using diluents or excipients such as fillers, extenders, binders, humectants, disintegrators, surfactants, etc. that are generally used. Formulations for parenteral administration include sterile aqueous solution, non-aqueous solvents, suspensions, emulsions, freeze-dried formulations, and suppositories. Propylene glycol, polyethylene glycol, vegetable oil such as olive oil, and injectable ester such as ethylolate, etc. may be used for non-aqueous solvents and suspensions. Witepsol, macrogol, tween 61, cacao butter, laurin butter, glycerogelatin, etc. may be used for a suppository base.

The present invention also provides an anticancer adjuvant comprising an inhibitor of the expression or activity of SH3RF2 protein.

The SH3RF2 protein may comprise, but not limited to, an amino acid sequence of SEQ ID NO:1.

The SH3RF2 protein expression inhibitor may be, but not limited to, any one selected from the group consisting of antisense nucleotides, small interfering RNAs (short interfering RNAs), and short hairpin RNAs, which bind complementarily to mRNA of SH3RF2 gene.

The SH3RF2 protein activity inhibitor may be, but not limited to, any one selected from the group consisting of compounds, peptides, peptide mimetics, aptamers, and antibodies, which bind complementarily to SH3RF2 protein.

The cancer may preferably be any one selected from the group consisting of liver cancer, colon cancer, cervical cancer, renal cancer, stomach cancer, prostate cancer, breast cancer, brain tumor, lung cancer, uterine cancer, colorectal cancer, bladder cancer, hematologic malignancy, and pancreatic cancer, and more preferably, it may be, but not limited to, liver cancer, colon cancer, cervical cancer, or renal cancer, and include any cancer caused by excessive expression or activity of SH3RF2.

SH3RF2, of which expression amount increases in various cancer tissues, binds to directly a cancer-associated gene, PAK4, and regulates the apoptosis-inhibitory function of PAK4 protein through the ubiquitination activity of SH3RF2 RING domain. Therefore, the cancer cells inhibited SH3RF2 expression respond so sensitively to the induction of apoptosis with simultaneous treatment of TNF-α and cycloheximide, which were reported as apoptosis inducers, to promote apoptosis and reduce in vivo tumorigenicity. Accordingly, inhibitors of the expression or activity of SH3RF2 protein can be used effectively for the anticancer adjuvant composition.

The present invention also provides a method for preventing cancers, comprising administering a pharmaceutical composition which comprises a pharmaceutically effective amount of an inhibitor of the expression or activity of SH3RF2 protein as an active ingredient to an individual.

Furthermore, the present invention provides a method for treating cancers, comprising administering a pharmaceutical composition which comprises a pharmaceutically effective amount of an inhibitor of the expression or activity of SH3RF2 protein as an active ingredient to an individual having cancer.

The pharmaceutically effect amount may be, but not limited to, from about 0.0001 to 100 mg/kg, preferably from about 0.001 to 10 mg/kg. The dose may be varied depending on body weight, age, gender, health condition, diet of a certain patient, administration period, administration method, clearance, severity of a disease, etc.

The pharmaceutical composition may be administered orally or parenterally upon clinical administration. For parenteral administration, it may be administered by intraperitoneal injection, intrarectal injection, subcutaneous injection, intravenous injection, intramuscular injection, dural injection, intracerebrovascular injection, or intrathoracic injection, and may be used in general medicine forms.

The cancer may preferably be any one selected from the group consisting of liver cancer, colon cancer, cervical cancer, renal cancer, stomach cancer, prostate cancer, breast cancer, brain tumor, lung cancer, uterine cancer, colorectal cancer, bladder cancer, hematologic malignancy, and pancreatic cancer, and more preferably, it may be, but not limited to, liver cancer, colon cancer, cervical cancer, or renal cancer, and include any cancer caused by excessive expression or activity of SH3RF2.

The individual may be vertebrate, preferably mammals, more preferably experimental animals, such as rats, rabbits, guinea pigs, hamsters, dogs, and cats, and most preferably anthropoids, such as chimpanzees and gorillas.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, inhibitors of the expression or activity of SH3RF2 protein can be used effectively for the prevention or treatment of cancers.

Furthermore, the present invention provides a method for screening candidate substances for an anticancer drug or anticancer adjuvant.

Specifically, the screening method may comprise:

(1) treating an SH3RF2 protein-expressing cell line with a test substance;

(2) measuring the level of expression or activity of SH3RF2 protein of the cell line; and (3) selecting the test substance which has the decreased level of expression or activity of SH3RF2 protein, compared to a control which was not treated with the test substance. However, the present invention is not limited thereto.

In the above method, the level of protein expression in step (2) may preferably be measured by any one selected from the group consisting of immunofluorescence, enzyme-linked immunosorbent assay (ELISA), Western Blot, and RT-PCR, and the level of protein activity may preferably be measured by any one selected from the group consisting of immunofluorescence, enzyme-linked immunosorbent assay (ELISA), mass spectrometry, and protein chip. However, the present invention is not limited thereto.

The screening method also may use the level of binding between SH3RF2 and PAK4.

Specifically, the screening method may comprise:

(1) bring SH3RF2 protein into contact with PAK4 protein under the presence of a test substance;

(2) measuring the level of binding between SH3RF2 protein and PAK4 protein; and (3) selecting the test substance which has the decreased level of binding between SH3RF2 protein and PAK4 protein, compared to a control which was not treated with the test substance. However, the present invention is not limited thereto.

The present inventors confirm that SH3RF2 and PAK4 bind directly together, and PAK4 binds to the second SH3 domain region in SH3RF2. Thus, this indicates that substances which inhibit the binding between SH3RF2 and PAK4 can inhibit the regulation of PAK4 expression, and be the substances having anticancer activity.

The level of binding may be measured by an immunoprecipitation method. Immunoprecipitation may be performed by a method in a document (Harlow and Lane, *Antibodies*, 511-52, Cold Spring Harbor Laboratory publications, New York, 1988). SDS-PAGE is generally used for analysis of immunoprecipitated proteins, and the bound proteins may be analyzed based on molecular weight of proteins using gel of a suitable concentration. In addition, a two-hybrid system, which uses cells, may be employed ("MATCHMAKER Two-Hybrid system", "MATCHMAKER Mammalian Two-Hybrid Assay Kit", "MATCHMAKER one-Hybrid system" (Clontech); "HybriZAP Two-Hybrid Vector System" (Stratagene); References-Dalton and Treisman, *Cell* 68: 597-612, 1992; Fields and Sternglanz, *Trends Genet.* 10: 286-92, 1994), and a biosensor using surface plasmon resonance phenomenon may be used as a means of detecting or quantifying the bound substances. When the biosensor is used, the binding-induced interaction may be observed as a surface plasmon resonance signal in real time.

Furthermore, the screening method may comprise:

(1) treating an SH3RF2 protein and ubiquitin protein-expressing cell line with a test substance;

(2) measuring the level of ubiquitination activity of SH3RF2 protein of the cell line; and (3) selecting the test substance which has the decreased level of ubiquitination activity of SH3RF2 protein, compared to a control which was not treated with the test substance. However, the present invention is not limited thereto.

In the screening method, the SH3RF2 protein may preferably comprise, but not limited to, an amino acid sequence of SEQ ID NO:1.

In the screening method, the candidate substance may preferably be any one selected from the group consisting of nucleic acids, proteins, other extracts, and natural substances; however, the present invention is not limited thereto.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, selecting a test substance which decreases the expression or activity of SH3RF2 protein, a test substance which inhibits the binding between SH3RF2 and PAK4, or a test substance which inhibits the ubiquitination of SH3RF2 can be used effectively for screening candidate substances for an anticancer drug or anticancer adjuvant.

The present invention also provides a method for promoting apoptosis, comprising treating hyperplastic cells with an inhibitor of the expression or activity of SH3RF2 protein.

The SH3RF2 protein may preferably comprise, but not limited to, an amino acid sequence of SEQ ID NO:1.

The SH3RF2 protein expression inhibitor may preferably be, but not limited to, any one selected from the group consisting of antisense nucleotides, small interfering RNAs (short interfering RNAs), and short hairpin RNAs, which bind complementarily to mRNA of SH3RF2 gene.

The SH3RF2 protein activity inhibitor may preferably be, but not limited to, any one selected from the group consisting of compounds, peptides, peptide mimetics, aptamers, and antibodies, which bind complementarily to SH3RF2 protein.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, inhibitors of the expression or activity of SH3RF2 protein can be used for promoting apoptosis of hyperplastic cells.

Furthermore, the present invention provides a method of decreasing PAK4 activity through inhibition of the expression or activity of SH3RF2 protein.

The SH3RF2 protein may preferably comprise, but not limited to, an amino acid sequence of SEQ ID NO:1.

The expression of SH3RF2 protein may preferably be inhibited by using any one selected from the group consisting of antisense nucleotides, small interfering RNAs (short interfering RNAs), and short hairpin RNAs, which bind complementarily to mRNA of SH3RF2 gene, however, the present invention is not limited thereto.

The activity of SH3RF2 protein may preferably be inhibited by using any one selected from the group consisting of compounds, peptides, peptide mimetics, aptamers, and antibodies, which bind complementarily to SH3RF2 protein, however, the present invention is not limited thereto.

The activity of SH3RF2 may preferably include, but is not limited to, the ubiquitination activity.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, inhibition of the expression or activity of SH3RF2 protein can be used effectively for decreasing the expression and activity of the oncogene, PAK4.

The present invention also provides a method for diagnosing cancers, identifying therapeutic results, or is assessing prognosis, the method comprising measuring SH3RF2 expression level in cancer cells, using any one or more of antibodies reactive with SH3RF2 protein or nucleic acids complementary to SH3RF2 gene.

The cancer may preferably be any one selected from the group consisting of liver cancer, colon cancer, cervical cancer, renal cancer, stomach cancer, prostate cancer, breast cancer, brain tumor, lung cancer, uterine cancer, colorectal cancer, bladder cancer, hematologic malignancy, and pancreatic cancer, and more preferably, it may be, but not limited to, liver cancer, colon cancer, cervical cancer, or renal cancer, and include all cancer caused by excessive expression or activity of SH3RF2.

According to the method for diagnosing cancers, detection of an elevated SH3RF2 expression higher than normal level tells that a patient has cancer. Furthermore, in a diagnosis reagent of an individual who has undergone or is undergoing cancer therapy, detection of a normal level of SH3RF2 expression tells a success of cancer therapy, and detection of an elevated SH3RF2 expression higher than normal level in the diagnosis reagent tells that cancer therapy should continue to be applied. Furthermore, in a diagnosis reagent of an individual having cancer, detection of a normal level of SH3RF2 expression tells that the prognosis is good; however, detection of an elevated SH3RF2 expression higher than normal level in the diagnosis reagent tells that the prognosis is bad.

Furthermore, the present invention provides a kit for diagnosing cancers, comprising any one or more of antibodies reactive with SH3RF2 protein or nucleic acids complementary to SH3RF2 gene.

The kit for diagnosing cancers may further comprise one or more substances which are reactive with SH3RF2, a reagent for detecting reaction products, and instructions related thereto. For example, one or more substances which are reactive with SH3RF2 may be an RNA or DNA complementary to RNA or DNA of SH3RF2, and an antibody which binds to an SH3RF2 protein. The reagent for detecting reaction products may be a nucleic acid or protein marker and a color reagent.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, antibodies reactive with SH3RF2 protein or nucleic acids complementary to SH3RF2 can be used effectively for the diagnosis of cancers and the kit for diagnosing cancers.

Furthermore, the present invention provides a use for utilizing an inhibitor of the expression or activity of SH3RF2 protein for preparation of a pharmaceutical composition for preventing or treating cancers.

The present invention also provides a use for utilizing an inhibitor of the expression or activity of SH3RF2 protein for preparation of an anticancer adjuvant.

The SH3RF2 protein may preferably comprise, but not limited to, an amino acid sequence of SEQ ID NO:1.

The SH3RF2 protein expression inhibitor may be, but not limited to, any one selected from the group consisting of antisense nucleotides, small interfering RNAs (short interfering RNAs), and short hairpin RNAs, which bind complementarily to mRNA of SH3RF2.

The SH3RF2 protein activity inhibitor may preferably be, but not limited to, any one selected from the group consisting of compounds, peptides, peptide mimetics, aptamers, and antibodies, which bind complementarily to SH3RF2 protein.

The cancer may preferably be any one selected from the group consisting of liver cancer, colon cancer, cervical cancer, renal cancer, stomach cancer, prostate cancer, breast cancer, brain tumor, lung cancer, uterine cancer, colorectal cancer, bladder cancer, hematologic malignancy, and pancreatic cancer, and more preferably, it may be, but not limited to, liver cancer, colon cancer, cervical cancer, or renal cancer, and include all cancer caused by excessive expression or activity of SH3RF2.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis with simultaneous treatment of TNF-α and cycloheximide, which were reported as apoptosis inducers, to promote apoptosis and reduce in vivo tumorigenicity. Accordingly, inhibitors of the expression or activity of SH3RF2 protein can be used effectively for preparation of pharmaceutical compositions for preventing or treating cancers, and anticancer adjuvants.

Furthermore, the present invention provides a use for utilizing an antibody reactive with SH3RF2 protein or a nucleic acid complementary to SH3RF2 gene for preparation of a kit for diagnosing cancers.

The kit for diagnosing cancers may further comprise one or more substances which are reactive with SH3RF2, a reagent for detecting reaction products, and instructions related thereto. For example, one or more substances which are reactive with SH3RF2 may be an RNA or DNA complementary to RNA or DNA of SH3RF2, and an antibody which binds to an SH3RF2 protein. The reagent for detecting reaction products may be a nucleic acid or protein marker and a color reagent.

SH3RF2, of which expression amount increases in various cancer tissues, binds to directly the cancer-associated gene, PAK4, and regulates the apoptosis-inhibitory function of PAK4 protein through the ubiquitination activity of SH3RF2 RING domain. Therefore, cancer cells which inhibited SH3RF2 expression respond so sensitively to the induction of apoptosis to promote apoptosis and reduce in vivo tumorigenicity. Accordingly, antibodies reactive with SH3RF2 protein or nucleic acids complementary to SH3RF2 can be used effectively for the diagnosis of cancers and preparation of the kit for diagnosing cancers.

Hereinafter, the present invention will be described in more detail with reference to examples and preparation examples.

However, the following examples and preparation examples are provided for illustrative purposes only, and the scope of the present invention should not be limited thereto.

EXAMPLE 1

Determination of SH3RF2 Expression Amount in Tumor Tissues

<1-1> Determination of SH3RF2 Expression Amount Using DNA Chip Analysis

SH3RF2 mRNA expression amount in tumor tissues or normal tissues of colon cancer tissues (obtained from Samsung medical center, Seoul, Korea) from 66 cases of colon cancer patients was analyzed using Sentrix BeadChip Array Human-6_V2 48K DNA chip (Illumines, Inc.).

Consequently, referring to FIG. 1A, SH3RF2 expression was increased about more than 1.5 times in 22 cases of tumor tissues among 66 cases of colon cancer tissues, compared to normal tissues.

<1-2> Determination of SH3RF2 Expression Amount Using Reverse Transcription-Polymerase Chain Reaction (RT-PCR)

20 cases of tumor tissues or normal tissues were randomly selected from total 66 cases of colon cancer tissues in Example <1-1>, and RT-PCR was carried out determine SH3RF2 mRNA expression amount. RT-PCR was carried out with cDNA synthesized from total RNAs, which were prepared by pulverizing each tissue and extracting with TRIZOL solution. 5 μg of the cDNA, forward primer for SH3RF2 mRNA (SEQ ID NO.3: 5'-GGTCCAAGCCTGCCCTCAC-3'), and reverse primer (SEQ ID NO.4: 5'-GGGTGGCTG-GCTGTTCAGG-3') were used. 0.5 μL of each primer (50 μmol/μL) was added, and 10 μL of 2×PCR PreMix (Bioneer, Inc., South Korea) and 3 μL of tissue cDNA were mixed thereto, and then distilled water was added thereto to bring the total volume up to 50 μL, and then the reaction mixture was made. PCR was carried out under the condition: 1 cycle of 94° C. for 4 min; 25 cycles of 95° C. for 30 sec, 58° C. for 30 sec, and 72° C. for 30 sec; and a final step of 94° C. for 30 sec, 58° C. for 30 sec, and 72° C. for 5 min. 10 μL aliquots were loaded onto a 1% of agarose gel.

Consequently, referring to FIG. 1B, SH3RF2 expression was increased in 12 cases of tumor tissues among the randomly selected 20 cases, compared to normal tissues.

<1-3> Determination of SH3RF2 Expression Amount Using Western Blotting

SH3RF2 protein expression amount was determined by carrying out Western blot analysis in various cancer cell lines such as the normal cell line, human lung fibroblast cell line IMR-90, and human liver cancer cell lines HepG2, PLC/PRF/5, and SK-Hep-1, human colon cancer cell lines SW620, SW480, and HT29, the human cervical cancer cell line HeLa, and the kidney cell line 293T. Specifically, the above cancer cell lines were lysed with 1×RIPA solution {20 mM Tris-HCl [pH 7.5], 150 mM sodium chloride, 1 mM EDTA, 1% NP-40 and 1× conc. protease inhibitor cocktail (Roche Inc., South Korea), 1× phosphatase inhibitor cocktail (Roche Inc., South Korea)}. Lysates which were obtained by centrifugation and removal of precipitates were quantified to the same amounts and analyzed by electrophoresis on 10% SDS-polyamide gel. SDS-polyamide gel was transferred electrically to a nitrocellulose transfer membrane (Whatman, Germany), and blocked with 5% skim milk for min. After blocking, anti-SH3RF2 monoclonal antibody (Abnova Cop., Taipei) diluted at 1:1000 was allowed to react for 16 hr. The above membrane was washed with 1×PBST for 30 min, and allowed to react with secondary mouse antibody (Abnova Cop, Taipei) diluted at 1:4000 for 1 hr. Proteins were detected using a chemiluminescence detection system (Thermo scientific).

Consequently, referring to FIG. 1C, a small amount of SH3RF2 protein was expressed in the normal cancer cell line (IMR-90), however, a remarkably large amount of SH3RF2 protein was expressed in most cancer cell lines, except for liver cancer cell lines.

EXAMPLE 2

Determination of an Ubiquitin Ligase Activity Domain in SH3RF2

<2-1> Preparation of SH3RF2 Mutants

SH3RF2 mutants were prepared by adding GST or Myc-epitope to N-terminal or C-terminal region respectively, in SH3RF2. Full-length form SH3RF2 gene was obtained by carrying out PCR. PCR template was cDNA, which was prepared by isolation from normal liver tissue. PCR was carried out with the PCR template, forward primer (SEQ ID NO.5: 5'-TTTTCTAGAATGGATGATTTGACGTTACTTG-3'), and reverse primer (SEQ ID NO:6: 5'-TTTGAAT-TCGTTTGCTGGGAAACACGGTCTGC-3'). 0.5 μL of each of the above primers (50 μmol/μL) was added, and 1 μL of PCR Tag polymerase (Elpis biotech Inc., South Korea), 10 μL of the reaction buffer (10×), 8 μL of 2.5 mM dNTP were mixed with 3 μL of template cDNA, and then distilled water was added thereto to bring the total volume up to 50 μL. PCR was carried out under the condition: 1 cycle of 94° C. for 4 min; 30 cycles of 95° C. for 30 sec, 60° C. for 30 sec, and 72° C. for 1 min and 30 sec; and a final step of 94° C. for 30 sec, 60° C. for 30 sec, and 72° C. for 5 min. For subcloning, the PCR products and a pcDNA3.1 (−)/myc-His A vector (pcDNA 3 vector having myc-his-tag, Invitrogen) were digested with XbaI/EcoRI and ligated at 16° C. for 2 hr using T4 DNA ligase (Fermentas Inc., USA). Each of SH3RF2 mutant gene expression vectors was obtained by using the above full-length form SH3RF2 gene expression vector as a template, and was subcloned such as the following method. Primers used herein were as in the following. 5'-TTTTCTA-GAATGGATGATTTGACGTTACTTG-3'(SEQ ID NO:7) and 5'-TTTGAATTCGGGATTCGGGGCACCGCAGC-3' (SEQ ID NO:8) were used for primers for a mutant having only RING domain (SH3RF2Δ1,2,3 SH3), and 5'-TTTTCTAGAATGCGAGCAAAGGCCTTATGC-3' (SEQ ID NO:9) and 5'-TTTGAATTCGTTTGCTGGGAAA-CACGGTCTGC-3'(SEQ ID NO:10) were used for primers for a mutant having no RING domain (SH3RF2ΔRING). SH3RF2 having Myc-epitope mutant expression vectors were prepared by inserting each of 6myc of PCR products, which were obtained by carrying out PCR with a template vector, pBS-9myc cassette vector (obtained from Seoul National University, South Korea), forward primer (SEQ ID NO:11: 5'-TTTAAGCTTGGTGAACAAAAGT-TGATTTCTGAAG-3') and reverse primer (SEQ ID NO.12: 5'-TTTAAGCTTTGGATCCGTTCAAGTCT-TCTTCTGAG-3'), into HindIII sites in SH3RF2 gene expression vectors.

<2-2> Preparation of SH3RF2 Mutant Recombinant Protein

To prepare a glutathione S-transferase (GST)-fused SH3RF2 mutant recombinant protein, PCR was carried out with the full-length SH3RF2 gene vector as a template using each primers for each mutants. Primers used herein were as in the following. 5'-TTGAATTCAAATGGATGATTTGACGT-TACTTG-3'(SEQ ID NO:13) and 5'-TTGTCGACT-CATTTGCTGGGAAACAC-3'(SEQ ID NO:14) were used for the full-length gene amplification; 5'-TTGAATTC-CCAACATTGAGGCGCTGC-3'(SEQ ID NO:15) and 5'-TTGTCGACTCATTTGCTGGGAAACAC-3'(SEQ ID NO:16) were used for the RING domain-deleted mutant (SH3RF2ΔRING) gene amplification; TTGAATTCCCAA-CATTGAGGCGCTGC-3'(SEQ ID NO:17) and 5'-TTGTC-GACTCAGAGCCAGGCAGACT-3'(SEQ ID NO:18) were used for the mutant consisting of the first and second SH3 domains (SH3RF2ΔRING 3 SH3) gene amplification; 5'-TTGAATTCTCCACATGGATGGGGTGCCTCG-3' (SEQ ID NO:19) and 5'-TTGTCGACTCACTGCG-GCAGCTGCTTGAT-3'(SEQ ID NO:20) were used for the mutant consisting of the first SH3 domain (SH3RF2ΔRING 2,3 SH3) gene amplification; 5'-TTGAATTCTCAAG-CAGCTGCCCCAGCCG-3'(SEQ ID NO:21) and 5'-TTGTCGACTCAAAGGTGTCTTGCGGTGAG-3'(SEQ ID NO:22) were used for the mutant consisting of the second SH3 domain (SH3RF2ΔRING 1,3 SH3) gene amplification; 5'-TTGAATTCCCGTGGTCAGTCTGCCTGG-3'(SEQ ID NO:23), and 5'-TTGTCGACTCATTTGCTGGGAAACAC-3'(SEQ ID NO:24) were used for the mutant consisting of the third SH3 domain (SH3RF2ΔRING 1,2 SH3) gene amplification; and 5'-TTGAATTCAAATGGATGATTTGACGT-TACTTG-3'(SEQ ID NO:25) and 5'-TTGTCGACTCAG-GAGCGCCTCA-3'(SEQ ID NO:26) were used for the mutant consisting of the RING domain (SH3RF2Δ1,2,3 SH3) gene amplification. Expression vectors for each DNA were prepared by cloning amplified each fragment into the EcoRI/SalI site in a pGEX-4T-2 vector (Invitrogen Inc., USA) in which the expression protein GST was inserted into the front site of multiple cloning site. 5 ml of LB culture medium added with ampicillin was incubated for 12 hr and inoculated again in 200 ml of LB culture medium added with ampicillin to incubate until the Optical Density at 600 nm of a spectrophotometer was 0.5. Then, 0.2 mM IPTG was added thereto, and incubation for 6 hr was done to induce the expression of recombinant proteins for each DNA fragment. Medium was removed by centrifugation. Medium-removed transfected cells for each derivative were suspended in 1×RIPA solution {20 mM Tris-HCl[pH 7.5], 150 mM sodium chloride, 1 mM EDTA, 1% NP-40 and 1× protease inhibitor cocktail (Roche Inc., South Korea), 1× phosphatase inhibitor cocktail (Roche Inc., South Korea)}, and cells were disrupted by sonication for 1 min. Disruption was repeated two times, and the precipitate was separated by centrifugation. SH3RF2 GST-fusion recombinant proteins were isolated and purified from the supernatant using glutathione sepharose 4B (GE Healthcare Life Science, USA).

<2-3> Measurement of the Ubiquitin Ligase Activity of SH3RF2 Mutants

A pcDNA-Ub-HA vector and pcDNA-SH3RF2-myc mutants were co-transplanted into HeLa cell lines, and immunoprecipitated with anti-c-myc monoclonal antibody (Santa cruz biotechnology INC., USA). To determine the ubiquitin protein, Western blotting was carried out with anti-HA monoclonal antibody (Covance Research Products Inc., USA).

Figure 2C:
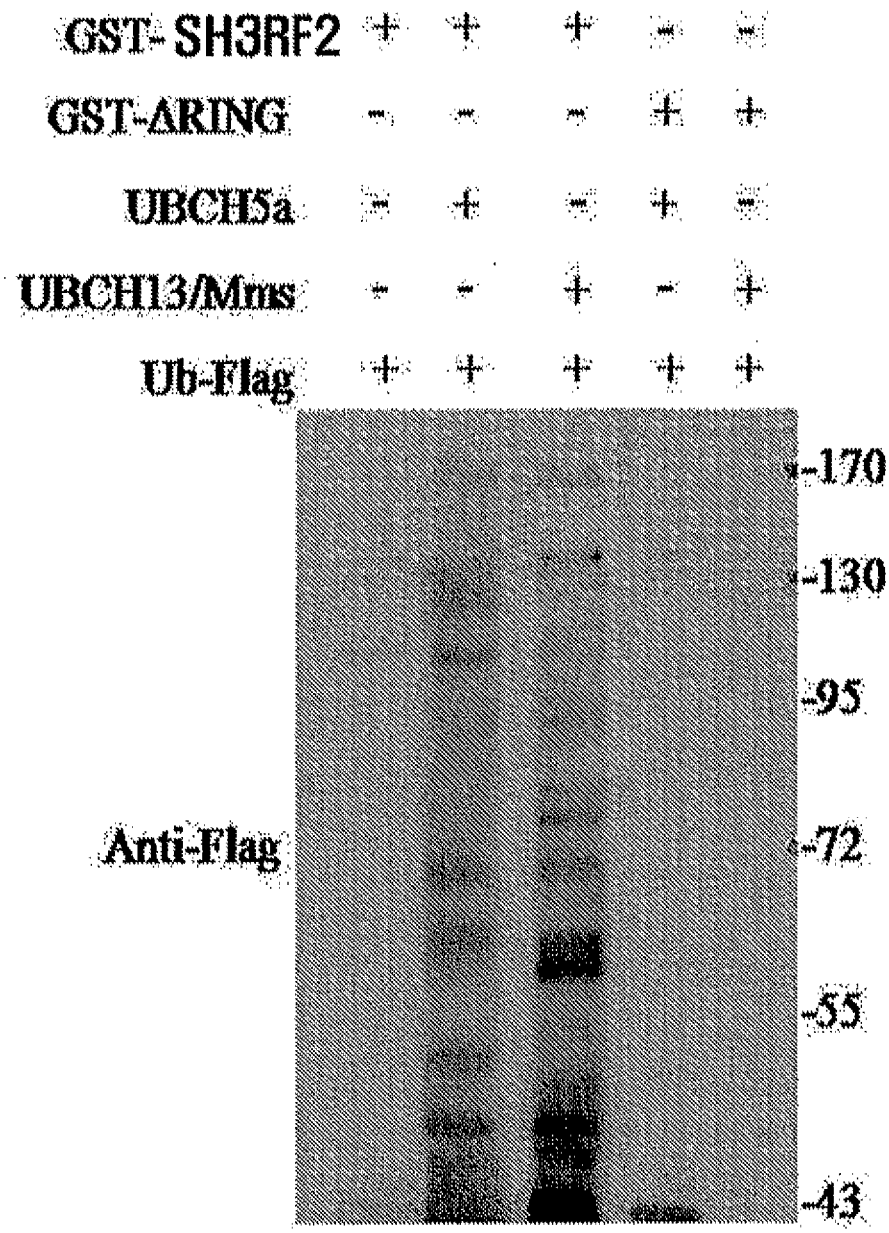
FIG. 2c: Self-ubiquitination activity for itself of SH3RF2 protein.

Consequently, referring to FIG. 2, transplantation of Myc-labelled SH3RF2 protein was identified with anti-Myc antibody, and by staining the Western blot membrane with Ponceau S staining, the amount of protein used for immunoprecipitation was identified to be the same. Anti-HA antibody bound, a high molecular weight, ubiquitinated SH3RF2 was found to be in the full-length SH3RF2 and pcDNA-Ub-HA-cotransplanted samples. SH3RF2 was found to be ubiquitinated also in samples cotransplanted with the mutant having no RING domain. However, ubiquitination was not found, or it was found to be very weak, in samples cotransplanted with only RING domain.

<2-4> Measurement of the Self-Ubiquitination Activity of SH3RF2 Mutants

The self-ubiquitination activity of SH3RF2 protein for itself was determined in vitro. UBCH5 and UBCH13/Mms, which were previously known to function mainly as E2 conjugating enzymes for E3 ligases having a RING domain, were used. 0.3 μM E2 enzyme UbCH5a conjugating enzyme (upstate, USA) and 50 nM Ubiquitin activating Enzyme E1 (upstate, USA) were mixed into ubiquitin reaction buffer {40 mM Tris-Hcl pH7.5, 1 mM DTT, 2 mM ATP, 5 mM MgCl2, 0.005% (v/v) Tween-20, Flag-Ubiquitin 1 μg/μl(Sigma, USA)}, and allowed to react with the full-length form SH3RF2 protein and SH3RF2ΔRING protein at 30° C. for 30 min, and then Western blotting was performed. To determine the ubiquitination activity using UbCH13/Mms2 conjugating enzyme (upstate, USA), UbCH13/Mms2 conjugating enzyme was allowed to react with the full-length form SH3RF2 protein and SH3RF2ΔRING protein using the ubiquitin reaction buffer according to the above method.

Consequently, the full-length SH3RF2 (GST-SH3RF2) having a RING domain showed E3 activity for UBCH5a or UBCH13/Mms E2, and the RING domain-deleted SH3RF2 mutant (GST-ΔRING) did not ubiquitinate itself. Results indicate that SH3RF2 is an E3 ligase having a RING domain which ubiquitinates itself.

EXAMPLE 3

Determination of the Interaction between p21-Activated Kinase 4 (PAK4) and SH3RF2 Protein <3-1> Determination of the Binding between PAK4 and SH3RF2

To determine whether the oncogene PAK4 protein, of which expression is increase in cancers and was reported to involve in inhibiting apoptosis and promoting cell migration, and SH3RF2 protein bind to each other, myc-labelled SH3RF2 gene expression vector, pcDNA-SH3RF2-myc, along with a pcDNA-PAK4-flag vector, were injected into HEK293T cell line (American Type Culture Collection, USA) at the same time, and after 48 hr, cytoplasm fraction was extracted and precipitated using anti-Flag mouse monoclonal antibody (SIGMA, USA), and then Western blotting was carried out with mouse anti-c-myc monoclonal antibody (Santa crux biotechnology INC., USA).

Consequently, referring to FIG. 3A, it was found that SH3RF2 protein and PAK4 protein bind to each other in cells.

<3-2> Determination of PAK Protein and SH3RF2 Protein

As confirmed in <Example 3-1>, PAK4 protein and SH3RF2 protein bind to each other in animal cells. The present inventors determined whether the binding is direct or indirect, and to which domain of SH3RF2 PAK4 binds. For determination, PAK4-His fusion recombinant protein and GST-SH3RF2 fusion recombinant protein were prepared by injecting a pET28a-PAK4-His vector or SH3RF2 mutant gene-cloned pGEX2T-SH3RF2 mutant vector into E. coli cell line BL21 (DE3) (Stratagene, USA), respectively. After the in vitro reaction between SH3RF2 mutant and PAK4, GST pull down was carried out using glutathione-agarose beads, and Western blotting was performed using anti-PAK4 polyclonal antibody (Cell Signaling technology, USA).

Consequently, referring to FIG. 3B, it was found that PAK4 His-fusion recombinant protein binds to the second SH3 domain in SH3RF2.

EXAMPLE 4

Determination of the Effect of Inhibition of SH3RF2 Expression on Apoptosis

<4-1> Induction of Apoptosis in HeLa Cell Line which Inhibited SH3RF2 Expression A previously published paper reported that PAK4 expression is involved in cancer apoptosis, and particularly, it was reported that apoptosis was promoted when cancer cells which inhibited PAK4 expression were treated with TNF-α and cycloheximide at the same time (Li X. & Minden A., *J Biol. Chem.* 2005, 280, 41192-41200).

Since it was found that SH3RF2 protein and the oncogene PAK4 protein bind to each other in <Example 3>, it was determined that the expression of SH3RF2 is associated with apoptosis caused by the simultaneous treatment of TNF-α and cycloheximide by carrying out the following experiment. SH3RF2 knock-downed HeLa cell line (HeLa/shSH3RF2#1 or HeLa/shSH3RF2 #3) (American Type Culture Collection, USA) or control (HeLa/shGFP) was treated with TNF-α and cycloheximide at the same time to induce apoptosis. After 4 hr of the induction of apoptosis, cell nucleus was observed by Hoechst staining and the number of stained cells was measured to quantify as percentage.

Consequently, referring to FIGS. 4A and 4B, the number of cells, of which nucleuses were stained bright by DNA condensation which occurs on apoptosis, in cells which inhibited SH3RF2 expression (shSH3RF2#1 or shSH3RF2#3) was remarkably greater than it was in control (HeLa/shGFP).

<4-2> Induction of Apoptosis in Liver Cancer Cell Line which Inhibited SH3RF2 Expression According to the method in <Example 4-1>, the effect of inhibition of SH3RF2 expression on apoptosis was determined using Huh 7 liver cancer cell line (American Type Culture Collection, USA), instead of HeLa cell line. SH3RF2 knock-downed Huh-7 cell line was prepared using a shSH3RF2 vector, and the above cells (shSH3RF2 #G6-7) were treated with TNF-α and cycloheximide at the same time to induce apoptosis. After hr of the induction of apoptosis, cell nucleuses were stained by Hoechst, and the number of Hoechst-stained bright cells by DNA condensation versus the total cell number was represented as a percentage graph.

Consequently, referring to FIGS. 4C and 4D, Huh7 cell line which SH3RF2 expression is inhibited also responded sensitively to apoptosis induced by the simultaneous treatment of TNF-α and cycloheximide.

<4-3> Measurement of Changes in Expression of Apoptotic Markers

Changes in expression of apoptotic markers by SH3RF2 gene knock-down were measured using Western blotting. SH3RF2 knock-downed HeLa cell lines {HeLa/shSH3RF2#1 or HeLa/shSH3RF2#3} in <Example 4-1> were treated with TNF-α and cycloheximide at the same time for 2, 3, or 4 hr, and then, cleaved caspase-8 and PARP protein, which are known as apoptotic markers, were determined by Western blotting using anti-cleaved PARP polyclonal antibody (Millipore, USA) or anti-caspase-8 monoclonal antibody (assay design inc., USA).

Consequently, referring to FIG. 5A, the level of expression of cleaved caspase-8 (p43, 43 kDa protein), the activated form of caspase-8, in HeLa cell line which SH3RF2 expression is inhibited was increased compared to control, and the level of expression of cleaved PARP was also increased. This result indicates that cells which SH3RF2 expression is inhibited respond more sensitively to apoptosis induced by TNF-α and cycloheximide treatment and apoptosis proceeds quickly.

<4-4> Measurement of Changes in Expression of Apoptotic Markers by SH3RF2 Overexpression In SK-Hep1 cancer cell line of which SH3RF2 expression amount is small (American Type Culture Collection, USA), SH3RF2 was allowed to be overexpressed, and the level of expression of cleaved PARP was measured according to Example <4-3>.

Consequently, referring to FIG. 5B, the change in the expression of cleaved PARP by TNF-α and cycloheximide was decreased in SH3RF2 overexpressed cell line compared to control, as opposed to cell line which inhibited SH3RF2 expression in <Example 4-2>. This indicates that overexpression of SH3RF2 increases the expression or activity of PAK4 so as to be resistant to apoptosis induced by TNF-α and cycloheximide, and thus, cleaved PARP is decreased compared to control.

<4-5> Determination of Change in c-Jun N-Terminal Kinase (JNK) Activity by Change in the Expression of SH3RF2

There is a report that PAK4 in <Example 3> is an upstream modulator of c-Jun N-terminal kinase (JNK) among MAP kinase pathway, and increases signals by tumor necrosis factor-α (TNF-α) (Gnesutta, N & Minden, A 2003). As a cellular reaction in response to stress, JNK, one of MAP kinases which are activated by MAPK kinase (MAPKK), phosphorylates c-Jun N-terminal region and regulates a transcription factor, activating protein-1 (AP-1). At this point, apoptosis is promoted by JNK1 activity, and it was reported that this mechanism of apoptosis is suppressed by JNK2 activity (Shafiq Uddin Ahmed & Jo Milner, PLoS ONE, 2009, Vol. 4, e7305).

Therefore, change in JNK activity induced by change in the expression of SH3RF2, which is involved in the regulation of apoptosis through the regulation of PAK4 expression amount, was measured using Western blotting. SH3RF2 knock-downed HeLa cell lines {HeLa/shSH3RF2#1 or HeLa/shSH3RF2#3} were treated with TNF-α and cycloheximide at the same time for 0, 15, 30, or 60 min, and phosphorylation of JNK was measured by Western blotting using anti-p-JNK polyclonal antibody (Santa cruz biotechnology INC., USA).

Consequently, referring to FIG. 5C, there were few changes in phosphorylation of JNK1, which induces the above apoptosis, in HeLa cell lines which inhibited SH3RF2 expression, however, phosphorylation of JNK2, which inhibits the mechanism of JNK1 which induces apoptosis, was decreased. Decrease in phosphorylation of JNK2 reduced phosphorylation of the downstream c-jun. Thus, it was found that the activity of AP-1, which consists of dimers of c-jun and c-fos, can be regulated by change in the expression amount of SH3RF2.

<4-6> Determination of Change in JNK Activity by Change in SH3RF2 Expression

Stabilized SH3RF2 overexpressed cell line prepared by injecting an SH3RF2 overexpression vector into SK-Hep1 cancer cell line, of which SH3RF2 expression amount is small, was treated with TNF-α and cycloheximide at the same time for 10, 20, or 30 min, and phosphorylation of JNK was determined by Western blotting.

Consequently, referring to FIG. 5D, there were no changes in phosphorylation of JNK1, and phosphorylation of JNK2 was increased. Increase in phosphorylation of JNK2 increases phosphorylation of the downstream c-jun. Thus, it was found that phosphorylation of JNK2 is regulated by SH3RF2, just as the results in <Example 4-5>.

<4-7> Determination of the Correlation between Difference in Sensitivity of Cancer Cells to Apoptosis Induced by TNF-α and SH3RF2 Protein To determine the effect of the level of SH3RF2 expression on the sensitivity or resistance of cancer cells to apoptosis induced by TNF-α, various cancer cell lines, which have different level of SH3RF2 expression, were treated with TNF-α and cycloheximide at the same time for 4 hr to induce apoptosis, and the activity of caspase-3/7 was measured using Apo-One Homogeneous caspase-3/7 Assay (Promega Co., #G7790) reagent.

Consequently, referring to FIG. 6a A, results indicate that apoptosis induced by TNF-α and cycloheximide treatment occurred in all cancer cell lines, and SK-Hep1 and Hep3B cell lines responded quite sensitively, and the other cell lines responded low at similar levels. From the result of FIG. 6a B, it was found that difference in sensitivity to apoptosis induced by TNF-α is related with SH3RF2 expression (FIG. 6a).

To verify this fact, SH3RF2 expression was suppressed in HeLa and Huh-7 cell lines, of which SH3RF2 expression is high, and SK-Hep1 and Hep3B cell lines, of which SH3RF2 expression is low, respectively, using SH3RF2 siRNA#05 (Thermo Scientific Dharmacon, Cat # J-007145-05). Control siRNA (QIAGEN, Cat #1027281) and SH3RF2 siRNA#06 (Thermo Scientific Dharmacon, Cat # J-007145-06) which has no or little expression inhibited effect were used for SH3RF2 expression inhibited controls.

Consequently, referring to FIG. 6b A, B, C, and D, there was no difference between before and after treatment in the activity of caspase-3/7 in siRNA control and the negative control, SH3RF2 siRNA#06. Increase in the activity of caspase-3/7 was remarkably great in cells treated with SH3RF2 siRNA#05 which knock-downs SH3RF2, compared to SH3RF2 expression inhibited controls. Increase in the activity of caspase-3/7 induced by inhibition of SH3RF2 expression was small in Huh7 (FIG. 6b A) and HeLa (FIG. 6b B) cell lines, of which SH3RF2 expression is high and the expression is not fully suppressed by siRNA, compared to that in SK-Hep1 (FIG. 6b C) and Hep3B (FIG. 6b D) cell lines, of which SH3RF2 expression is low. Therefore, it was found that SH3RF2 has a function to protect cells from TNF-α-induced apoptosis.

EXAMPLE 5

Determination of the Effect of PAK4 Expression in Accordance with Change in the Expression Amount of SH3RE2

<5-1> Determination of PAK4 Protein Expression Amount

PAK4 protein expression amount in the above SH3RF2 overexpressed cell line or knock-down cell line was determined by Western blotting using anti-PAK4 polyclonal antibody (Cell Signaling technology, USA).

Consequently, referring to FIG. 7A, the amount of PAK4 protein was increased in SH3RF2 overexpressed cell line. On the contrary, the amount of PAK4 protein was decreased in cell line which inhibited SH3RF2 expression.

To determine whether this change in the amount of PAK4 protein in SH3RF2 overexpressed cell line is induced by temporary SH3RF2 expression or not, an SH3RF2 expression vector was injected into HEK293T or HeLa cell lines, and after 48 hr, PAK4 protein present in cells was determined using PAK4 antibody.

Consequently, referring to FIG. 7B, it was found that the amount of PAK4 protein was increased in the cell line, which overexpresses SH3RF2 continuously. However, there was no change in PAK4 protein in RING domain-deleted, SH3RF2 overexpressed cell line having no ubiquitination activity. Therefore, it is found that the ubiquitination activity is required for the regulation of the expression amount of PAK4.

<5-2> Determination of the Expression of PAK4 Gene

Referring to <Example 5-1>, to determine whether the regulation of PAK4 expression by change in SH3RF2 expression is by the regulation of gene transcription or by the regulation of gene post-transcription, PAK4 mRNA expression was determined by RT-PCR. Primers used herein were as follows: forward primer was 5'-GAGCTGCTCTTCAAC-CAGGT-3'(SEQ ID NO:27); and reverse primer was 5'-CTC-CTCGTTCATCCTGGTGT-3'(SEQ ID NO:28).

Consequently, referring to FIG. 7C, there was no change in the expression amount of PAK4 mRNA.

EXAMPLE 6

Determination of Tumorigenicity in vivo in Accordance with the Expression Amount of SH3RF2

<6-1> Determination of Tumorigenicity of SH3RF2 Knock-Downed Cell Line in a Mouse Cell fractions were extracted from each colony cell line (sh SH3RF2 G6-2, G6-4, G6-5 or G6-7) wherein SH3RF2 was knock-downed using a lentiviral vector in Huh-7 liver cancer cell line, and Western blotting was performed. Consequently, referring to FIG. 8A, it was found that the expression of SH3RF2 protein was effectively inhibited. Among the above SH3RF2 knock-down cells, shSH3RF2 G6-7 cell line or control (shControl) cell line were injected into a nude mouse (athymic nu/nu on BALB/c background; Japan) respectively, and 23 days later, tumorigenicity was compared.

Consequently, referring to FIG. 8B, the size of tumors which were formed in the nude mouse injected with Huh-7 cells or control (shControl) cell line was similar, however, the size of tumor which was formed in the nude mouse injected with shSH3RF2 G6-7 cell line, of which SH3RF2 was knock-downed, was remarkably small compared to control.

<6-2> Determination of Tumorigenicity of SH3RF2 Overexpressed Cell Line in a Mouse Proteins were extracted from SH3RF2-myc #3 colony cells which is myc-labelled SH3RF2-overexpressing PLC/PRF/5 liver cancer cell line (American Type Culture Collection, USA), or control (pcDNA) cells to perform Western blotting. Consequently, referring to FIG. 7C, it was found that the expression of SH3RF2 protein was effectively overexpressed. The above SH3RF2-myc #3 colony cells or control (pcDNA) cells were injected into a nude mouse, and 45 days later, tumorigenicity was compared.

Consequently, referring to FIG. 8C, tumor was not formed in the nude mouse injected with control (pcDNA) cells, however, tumor was formed in 4 of 5 nude mice injected with SH3RF2-myc #3 colony cells, of which SH3RF2 was overexpressed. Therefore, it was found that SH3RF2 is an oncogene, and when SH3RF2 is deficient, tumor formation decreases, and when SH3RF2 is overexpressed, tumor formation increases.

EXAMPLE 7

Determination of SH3RF2 Protein Expression in Liver Cancer Tissues or Normal Liver Tissues To determine the expression pattern of SH3RF2 protein in clinical tissues, SH3RF2 protein expression was determined using tissue microarray (TMA) which consisted of liver cancer clinical tissues from 104 cases of liver cancer patients diagnosed at Inje University Paik Hospital, or 24 cases of normal liver tissues, and was prepared. Each tissue harvested was fixed with 10% formalin to prepare a paraffin block {paraffin-embedded HCC (donor block)}. Core tissue biopsy (2 mm in diameter) was taken from the paraffin block and arranged in a recipient paraffin block (tissue array block) using a trephine apparatus (Superbiochips Laboratories, Korea) to prepare tissue microarray. From the above tissue array block, an immunohistochemical experiment was carried out. Specifically, after deparaffining and antigenic retrieval processes, a slide was labeled with anti-SH3RF2 antibody (1:100), and labeled SH3RF2 was analyzed by avidin-biotin complex (ABC) method. Herein, 3,3'-Diaminobenzidine (DAB) was used for a chromogen. Saline solution was used for a negative control for the antibody, and in tissue area, when more than 10% of cells were uniformly stained, it was regarded as positive.

Consequently, referring to FIG. 9a, FIG. 9b, and FIG. 9c, the expression of SH3RF2 protein was not found in normal liver tissues, however, the expression was found only in vascular endothelial-myocytes. However, in case of liver cancer tissues, SH3RF2 expression was found in 43 of 104 cases of liver cancer tissues, and most SH3RF2 proteins expressed (40 cases) existed in nucleus, and in 2 cases, proteins were expressed in cytoplasm and in the other 1 case, proteins existed in cell membrane. As a result of a comparative analysis of the above TMA results and clinical data of cancer patients, there was a significant relationship (p<0.05) between SH3RF2 expression and patient's age, the progression stage, type of metastasis, or recurrence of cancer, and SH3RF2 expression was also closely related to patient's survival (P=0.0149).

PREPARATION EXAMPLE 1

Preparation of Pharmaceutical Compositions

<1-1> Powder Preparation
Inhibitors of the expression or activity of SH3RF2 protein 2 g
Lactose 1 g
The above ingredients were mixed, and filled into an airtight bag to prepare a powder.

<1-2> Tablet Preparation
Inhibitors of the expression or activity of SH3RF2 protein 100 mg
Corn starch 100 mg
Lactose 100 mg
Magnesium stearate 2 mg
The above ingredients were mixed, and tabletted according to a conventional tablet preparation method to prepare a tablet.

<1-3> Capsule Preparation
Inhibitors of the expression or activity of SH3RF2 protein 100 mg
Corn starch 100 mg
Lactose 100 mg
Magnesium stearate 2 mg
The above ingredients were mixed, and filled in a gelatin capsule according to a conventional capsule preparation method to prepare a capsule.

<1-4> Pill Preparation
Inhibitors of the expression or activity of SH3RF2 protein 1 g
Lactose 1.5 g
Glycerin 1 g
Xylitol 0.5 g
The above ingredients were mixed to prepare a pill (4 g per pill) according to a conventional pill preparation method.

<1-5> Granule Preparation
Inhibitors of the expression or activity of SH3RF2 protein 150 mg
Soybean extracts 50 mg
Glucose 200 mg
Starch 600 mg
The above ingredients were mixed, 100 mg of 30% ethanol was added thereto, and the mixture was dried at 60° C. to form granules, and then filled into a bag.

As stated above, inhibitors of the expression or activity of SH3RF2 protein promote apoptosis and decrease tumorigenicity, and thus, can be used effectively for an anticancer pharmaceutical composition for preventing or treating cancers, for an anticancer adjuvant for anticancer compounds, for exploration of candidate substances for an anticancer drug, or for diagnosing cancers which are caused by overexpression of SH3RF2.

What is claimed is:

1. A method for inhibiting expression or activity of a PAK4 (P21-activating kinase 4) in a cancer cell, said method comprising:
   (i) introducing an effective amount of an inhibitor of the expression or activity of SH3RF2 (SH domain containing ring finger 2) protein into the cancer cell, and
   (ii) measuring an expression or activity level of PAK4 in the cell of step (i); wherein the inhibitor of the expression of SH3RF2 protein is any one selected from the group consisting of antisense nucleotides, small interfering RNAs (short interfering RNAs), and short hairpin RNAs, which bind complementarily to mRNA of SH3RF2 gene.

2. The method according to claim 1, wherein SH3RF2 protein comprises an amino acid sequence of SEQ ID NO:1.

3. The method according to claim 1, wherein the cancer cell is any one selected from the group consisting of liver cancer cell, colon cancer cell, cervical cancer cell, renal cancer cell, stomach cancer cell, prostate cancer cell, breast cancer cell, brain tumor cell, lung cancer cell, uterine cancer cell, colorectal cancer cell, bladder cancer cell, hematologic malignancy cell, and pancreatic cancer cell.

4. The method according to claim 1, wherein the inhibitor of the expression or activity of SH3RF2 protein decreases the level of binding between SH3RF2 protein and PAK4 protein.

5. The method according to claim 1, wherein the inhibitor of the expresssion or activity of SH3RF2 protein decrease the level of ubiquitination activity of SH3RF2 protein.

* * * * *

SEQUENCE LISTING

```
<160> NUMBER OF SEQ ID NOS: 28

<210> SEQ ID NO 1
<211> LENGTH: 729
<212> TYPE: PRT
<213> ORGANISM: Homo sapiens

<400> SEQUENCE: 1

Met Asp Asp Leu Thr Leu Leu Asp Leu Leu Glu Cys Pro Val Cys Phe
 1               5                  10                  15

Glu Lys Leu Asp Val Thr Ala Lys Val Leu Pro Cys Gln His Thr Phe
            20                  25                  30

Cys Lys Pro Cys Leu Gln Arg Val Phe Lys Ala His Lys Glu Leu Arg
        35                  40                  45

Cys Pro Glu Cys Arg Thr Pro Val Phe Ser Asn Ile Glu Ala Leu Pro
    50                  55                  60
```

```
Ala Asn Leu Leu Leu Val Arg Leu Leu Asp Gly Val Arg Ser Gly Gln
 65                  70                  75                  80

Ser Ser Gly Arg Gly Ser Phe Arg Arg Pro Gly Thr Met Thr Leu
                 85                  90                  95

Gln Asp Gly Arg Lys Ser Arg Thr Asn Pro Arg Arg Leu Gln Ala Ser
                100                 105                 110

Pro Phe Arg Leu Val Pro Asn Val Arg Ile His Met Asp Gly Val Pro
            115                 120                 125

Arg Ala Lys Ala Leu Cys Asn Tyr Arg Gly Gln Asn Pro Gly Asp Leu
        130                 135                 140

Arg Phe Asn Lys Gly Asp Ile Ile Leu Arg Arg Gln Leu Asp Glu
145                 150                 155                 160

Asn Trp Tyr Gln Gly Glu Ile Asn Gly Ile Ser Gly Asn Phe Pro Ala
                165                 170                 175

Ser Ser Val Glu Val Ile Lys Gln Leu Pro Gln Pro Pro Leu Cys
            180                 185                 190

Arg Ala Leu Tyr Asn Phe Asp Leu Arg Gly Lys Asp Lys Ser Glu Asn
        195                 200                 205

Gln Asp Cys Leu Thr Phe Leu Lys Asp Asp Ile Ile Thr Val Ile Ser
210                 215                 220

Arg Val Asp Glu Asn Trp Ala Glu Gly Lys Leu Gly Asp Lys Val Gly
225                 230                 235                 240

Ile Phe Pro Ile Leu Phe Val Glu Pro Asn Leu Thr Ala Arg His Leu
                245                 250                 255

Leu Glu Lys Asn Lys Gly Arg Gln Ser Ser Cys Thr Lys Asn Leu Ser
            260                 265                 270

Leu Val Ser Ser Ser Arg Gly Asn Thr Thr Leu Arg Arg Gly
        275                 280                 285

Pro Gly Ser Arg Arg Lys Val Pro Gly Gln Phe Ser Ile Thr Thr Ala
        290                 295                 300

Leu Asn Thr Leu Asn Arg Met Val His Ser Pro Ser Gly Arg His Met
305                 310                 315                 320

Val Glu Ile Ser Thr Pro Val Leu Ile Ser Ser Ser Asn Pro Ser Val
                325                 330                 335

Ile Thr Gln Pro Met Glu Lys Ala Asp Val Pro Ser Ser Cys Val Gly
            340                 345                 350

Gln Val Ser Thr Tyr His Pro Ala Pro Val Ser Pro Gly His Ser Thr
        355                 360                 365

Ala Val Val Ser Leu Pro Gly Ser Gln Gln His Leu Ser Ala Asn Met
        370                 375                 380

Phe Val Ala Leu His Ser Tyr Ser Ala His Gly Pro Asp Glu Leu Asp
385                 390                 395                 400

Leu Gln Lys Gly Glu Gly Val Arg Val Leu Gly Lys Cys Gln Asp Gly
                405                 410                 415

Trp Leu Arg Gly Val Ser Leu Val Thr Gly Arg Val Gly Ile Phe Pro
            420                 425                 430

Asn Asn Tyr Val Ile Pro Ile Phe Arg Lys Thr Ser Ser Phe Pro Asp
        435                 440                 445

Ser Arg Ser Pro Gly Leu Tyr Thr Thr Trp Thr Leu Ser Thr Ser Ser
        450                 455                 460

Val Ser Ser Gln Gly Ser Ile Ser Glu Gly Asp Pro Arg Gln Ser Arg
465                 470                 475                 480

Pro Phe Lys Ser Val Phe Val Pro Thr Ala Ile Val Asn Pro Val Arg
```

```
            485             490             495
Ser Thr Ala Gly Pro Gly Thr Leu Gly Gln Gly Ser Leu Arg Lys Gly
            500             505             510

Arg Ser Ser Met Arg Lys Asn Gly Ser Leu Gln Arg Pro Leu Gln Ser
            515             520             525

Gly Ile Pro Thr Leu Val Val Gly Ser Leu Arg Arg Ser Pro Thr Met
            530             535             540

Val Leu Arg Pro Gln Gln Phe Gln Phe Tyr Gln Pro Gln Gly Ile Pro
545             550             555             560

Ser Ser Pro Ser Ala Val Val Glu Met Gly Ser Lys Pro Ala Leu
            565             570             575

Thr Gly Glu Pro Ala Leu Thr Cys Ile Ser Arg Gly Ser Glu Ala Arg
            580             585             590

Ile His Ser Ala Ala Ser Ser Leu Ile Met Glu Asp Lys Glu Ile Pro
            595             600             605

Ile Lys Ser Glu Pro Leu Pro Lys Pro Pro Ala Ser Ala Pro Pro Ser
            610             615             620

Ile Leu Val Lys Pro Glu Asn Ser Arg Asn Gly Ile Glu Lys Gln Val
625             630             635             640

Lys Thr Val Arg Phe Gln Asn Tyr Ser Pro Pro Thr Lys His Tyr
            645             650             655

Thr Ser His Pro Thr Ser Gly Lys Pro Glu Gln Pro Ala Thr Leu Lys
            660             665             670

Ala Ser Gln Pro Glu Ala Ala Ser Leu Gly Pro Glu Met Thr Val Leu
            675             680             685

Phe Ala His Arg Ser Gly Cys His Ser Gly Gln Gln Thr Asp Leu Arg
690             695             700

Arg Lys Ser Ala Leu Ala Lys Ala Thr Thr Leu Val Ser Thr Ala Ser
705             710             715             720

Gly Thr Gln Thr Val Phe Pro Ser Lys
            725

<210> SEQ ID NO 2
<211> LENGTH: 3019
<212> TYPE: DNA
<213> ORGANISM: Homo sapiens

<400> SEQUENCE: 2
aaagcggttg gcagcagcgg cgcttggagg aaaggaagcc ggttggaggg cgcagcgcac      60
ccctgctgcg cggaggaggg ggctgagctg aactcagcag aagttacatg cacaaggcaa     120
aaattctgac gttctcaaga gaccagctct gcccccgtgg ctcaactgac cctaccatgt     180
ggacgctgct cctccaggtg ggaactggag ttttgaaata aaatggatga tttgacgtta     240
cttgatcttc tggagtgccc tgtgtgcttt gagaagctcg atgtcacagc caaagtcctc     300
ccttgccagc acaccttctg caaaccatgt ctacagaggg ttttcaaggc ccacaaagag     360
ctgcggtgcc ccgaatgcag gacgcctgtg ttttccaaca ttgaggcgct gccggccaac     420
ctgctgctcg tgcgccttct ggatggagtg cgctcagggc agagctccgg gagaggggc      480 tccttccgca ggcctggcac gatgaccttg caggatggca ggaaaagcag gaccaacccc     540
agacgtctgc aggccagtcc tttccggcta gtgcctaatg tcagaatcca catggatggg     600
gtgcctcgag caaaggcctt atgcaactac agagggcaga atcccggtga cctaaggttt     660
aataagggag atatcatcct tctccggaga cagcttgatg agaattggta ccaggggaa      720
```

```
atcaatggca tcagcgggaa cttcccagcc agctccgtgg aagtcatcaa gcagctgccc      780
cagccgcccc cgctctgcag ggccctctac aacttcgacc tacgaggcaa ggacaagagt      840
gagaaccagg attgcctgac cttcctcaag gacgatatca tcactgtgat cagccgagtg      900
gatgagaact gggcagaagg caagttagga gataaagtag gcatcttccc tatcttgttt      960
gtagagccaa acctcaccgc aagacacctt ttagagaaga acaaaggtcg ccagtcatcc     1020
tgcacaaaaa acctgtccct ggtgtcctcg tcctccagag gcaacacgtc taccctccgt     1080
aggggcccag gtccaggag gaaggtgcct gggcagtttt ccatcacaac agccttgaac     1140
actctcaacc ggatggtcca ttctccttca gggcgccata tggtagagat cagcacccca     1200
gtgctcatca gctccagcaa cccctctgtg atcacccagc catggagaa agcagacgtt     1260
ccttccagct gtgtgggaca ggtcagcact tatcaccccg cacctgtctc tccaggacat     1320
tccacagccg tggtcagtct gcctggctcc cagcaacacc tctcagcgaa catgtttgta     1380
gccctgcact cctactcagc ccatggaccc gatgagctgg acctgcaaaa gggagaaggc     1440
gtcagggtcc tggggaagtg ccaggacggc tggctcaggg gcgtctcctt ggtcaccggg     1500
cgagtcggca tcttcccaaa caattacgtc atccccattt tcagaaagac ctctagtttt     1560
ccagactccc ggagccctgg tctctacacc acatggacgt tatccacctc ctctgtgtcc     1620
tcccaaggca gcatttcaga aggtgatcca cggcaaagcc gtcccttcaa atccgtcttt     1680
gtgcccactg ccatagtcaa ccccgtgaga agcacagccg ccctgggac tttaggacaa     1740
gggtctcttc ggaaagggcg gagcagcatg agaaagaatg gatccctgca gagacccctc     1800
cagtccggga tccccactct cgtggtaggc tccctcagac gcagcccac catggtcctt     1860
cggcctcagc agttccaatt ctaccagcca caggggatcc cctcctcccc ctcagccgtg     1920
gtggtggaga tgggggtccaa gcctgccctc acggggggagc ccgccctcac gtgcatcagc     1980
aggggcagtg aggcccggat ccactccgcg gccagctccc tcattatgga agacaaagaa     2040
atccccatca gagtgagcc tctgccaaaa ccgcccgcat ctgccccacc atccatcctg     2100
gtgaaaccag aaaactcaag aaatggcatc gaaaagcaag tcaaaaccgt gagatttcag     2160
aattacagcc ctcctcccac caaacattac acctcccatc ccacctccgg aaagcctgaa     2220
cagccagcca ccctcaaggc gtcccagcct gaagcagcgt ccttgggccc agagatgacc     2280
gtcctatttg cccaccgaag tggctgccac tccggacagc agacagacct ccggagaaag     2340
tcagctcttg ccaaggccac aaccctggtg tccactgcct caggcacgca gaccgtgttt     2400
cccagcaaat gaacctacgg gtggcttttc ctagaccca aagaggtgaa ttgcattaa     2460
atacagtctg cctccactga gggcatcctg ccattctttg gggacttgag catgggtcct     2520
tgttcttcct atttcacctc caggaaagca aaagtgggag cagaaattcc tgccctgggt     2580
gggaggatag atggcgtggc cttccaaaca tacaaacata atgatttgat gccacaaagc     2640
tcgcttactc agaccaagga gtgaaaaatt gtcgtgccca ctttatgccc cagcatggag     2700
tatgtggcct cttgtcatcc ccgtgttact gtgtagaatt tctatggtgt cctaaagggg     2760
gctgcagcag gggtgtgaca acggtgggat tgttggcgtt gcttctttga ccttacaata     2820
tcctcaacaa gcattagaac aacttctgcc atcttctggg gcctgtacac tggccactag     2880
tagctgccat atctttttcc ctctgtaaag tcataatcct ggctgcaaag ggaggatttc     2940
tgcgcggggt gtgaggtgga tactttgaac attctgagaa cccaataaaa ctagaaggag     3000
ccaaaaaaaa aaaaaaaa                                                   3019
```

<210> SEQ ID NO 3
<211> LENGTH: 19
<212> TYPE: DNA
<213> ORGANISM: Artificial Sequence
<220> FEATURE:
<223> OTHER INFORMATION: To determine SH3RF2 mRNA expression amount in colon cancer tissues, forward primer for SH3RF2 mRNA for RT-PCR were used.

<400> SEQUENCE: 3
ggtccaagcc tgccctcac                                        19

<210> SEQ ID NO 4
<211> LENGTH: 19
<212> TYPE: DNA
<213> ORGANISM: Artificial Sequence
<220> FEATURE:
<223> OTHER INFORMATION: To determine SH3RF2 mRNA expression amount in colon caner tissues, reverse primer for RT-PCR were used.

<400> SEQUENCE: 4
gggtggctgg ctgttcagg                                        19

<210> SEQ ID NO 5
<211> LENGTH: 31
<212> TYPE: DNA
<213> ORGANISM: Artificial Sequence
<220> FEATURE:
<223> OTHER INFORMATION: Forward primer for obtain full-length form SH3RF2 gene by using PCR.

<400> SEQUENCE: 5
ttttctagaa tggatgattt gacgttactt g                          31

<210> SEQ ID NO 6
<211> LENGTH: 32
<212> TYPE: DNA
<213> ORGANISM: Artificial Sequence
<220> FEATURE:
<223> OTHER INFORMATION: Reverse primer for obtain full-length form SH3RF2 gene by using PCR.

<400> SEQUENCE: 6
tttgaattcg tttgctggga aacacggtct gc                         32

<210> SEQ ID NO 7
<211> LENGTH: 31
<212> TYPE: DNA
<213> ORGANISM: Artificial Sequence
<220> FEATURE:
<223> OTHER INFORMATION: SH3RF2 1,2,3 SH3 forward primer

<400> SEQUENCE: 7
ttttctagaa tggatgattt gacgttactt g                          31

<210> SEQ ID NO 8
<211> LENGTH: 29
<212> TYPE: DNA
<213> ORGANISM: Artificial Sequence
<220> FEATURE:
<223> OTHER INFORMATION: SH3RF2 1,2,3 SH3 reverse primer

<400> SEQUENCE: 8
tttgaattcg gcattcgggg caccgcagc                             29

<210> SEQ ID NO 9
<211> LENGTH: 30

-continued

```
<212> TYPE: DNA
<213> ORGANISM: Artificial Sequence
<220> FEATURE:
<223> OTHER INFORMATION: SH3RF2 RING forward primer.

<400> SEQUENCE: 9
ttttctagaa tgcgagcaaa ggccttatgc                               30

<210> SEQ ID NO 10
<211> LENGTH: 32
<212> TYPE: DNA
<213> ORGANISM: Artificial Sequence
<220> FEATURE:
<223> OTHER INFORMATION: SH3RF2 RING reverse primer

<400> SEQUENCE: 10
tttgaattcg tttgctggga aacacggtct gc                            32

<210> SEQ ID NO 11
<211> LENGTH: 34
<212> TYPE: DNA
<213> ORGANISM: Artificial Sequence
<220> FEATURE:
<223> OTHER INFORMATION: Myc-epitope forward primer

<400> SEQUENCE: 11
tttaagcttg gtgaacaaaa gttgatttct gaag                          34

<210> SEQ ID NO 12
<211> LENGTH: 35
<212> TYPE: DNA
<213> ORGANISM: Artificial Sequence
<220> FEATURE:
<223> OTHER INFORMATION: Myc-epitope reverse primer

<400> SEQUENCE: 12
tttaagcttt ggatccgttc aagtcttctt ctgag                         35

<210> SEQ ID NO 13
<211> LENGTH: 32
<212> TYPE: DNA
<213> ORGANISM: Artificial Sequence
<220> FEATURE:
<223> OTHER INFORMATION: full-length form SH3RF2 forward primer for
      full-length gene amplification

<400> SEQUENCE: 13
ttgaattcaa atggatgatt tgacgttact tg                            32

<210> SEQ ID NO 14
<211> LENGTH: 26
<212> TYPE: DNA
<213> ORGANISM: Artificial Sequence
<220> FEATURE:
<223> OTHER INFORMATION: full-length form SH3RF2 reverse primer for
      full-length gene amplification

<400> SEQUENCE: 14
ttgtcgactc atttgctggg aaacac                                   26

<210> SEQ ID NO 15
<211> LENGTH: 26
<212> TYPE: DNA
<213> ORGANISM: Artificial Sequence
<220> FEATURE:
<223> OTHER INFORMATION: SH3RF2 RING forward primer for the RING
      domain-deleted mutant gene amplification
```

```
<400> SEQUENCE: 15
ttgaattccc aacattgagg cgctgc                                              26

<210> SEQ ID NO 16
<211> LENGTH: 26
<212> TYPE: DNA
<213> ORGANISM: Artificial Sequence
<220> FEATURE:
<223> OTHER INFORMATION: SH3RF2 RING reverse primer for the RING
      domain-deleted mutant gene amplification

<400> SEQUENCE: 16
ttgtcgactc atttgctggg aaacac                                              26

<210> SEQ ID NO 17
<211> LENGTH: 26
<212> TYPE: DNA
<213> ORGANISM: Artificial Sequence
<220> FEATURE:
<223> OTHER INFORMATION: SH3RF2 RING 3 SH3 forward primer

<400> SEQUENCE: 17
ttgaattccc aacattgagg cgctgc                                              26

<210> SEQ ID NO 18
<211> LENGTH: 25
<212> TYPE: DNA
<213> ORGANISM: Artificial Sequence
<220> FEATURE:
<223> OTHER INFORMATION: SH3RF2 RING 3 SH3 reverse primer

<400> SEQUENCE: 18
ttgtcgactc agagccaggc agact                                               25

<210> SEQ ID NO 19
<211> LENGTH: 30
<212> TYPE: DNA
<213> ORGANISM: Artificial Sequence
<220> FEATURE:
<223> OTHER INFORMATION: SH3RF2 RING 2,3 SH3 forward primer

<400> SEQUENCE: 19
ttgaattctc cacatggatg gggtgcctcg                                          30

<210> SEQ ID NO 20
<211> LENGTH: 29
<212> TYPE: DNA
<213> ORGANISM: Artificial Sequence
<220> FEATURE:
<223> OTHER INFORMATION: SH3RF2 RING 2,3 SH3 reverse primer

<400> SEQUENCE: 20
ttgtcgactc actggggcag ctgcttgat                                           29

<210> SEQ ID NO 21
<211> LENGTH: 28
<212> TYPE: DNA
<213> ORGANISM: Artificial Sequence
<220> FEATURE:
<223> OTHER INFORMATION: SH3RF2 RING 1,3 SH3 forward primer

<400> SEQUENCE: 21
ttgaattctc aagcagctgc cccagccg                                            28
```

```
<210> SEQ ID NO 22
<211> LENGTH: 29
<212> TYPE: DNA
<213> ORGANISM: Artificial Sequence
<220> FEATURE:
<223> OTHER INFORMATION: SH3RF2 RING 1,3 SH3 reverse primer

<400> SEQUENCE: 22
ttgtcgactc aaaggtgtct tgcggtgag                                     29

<210> SEQ ID NO 23
<211> LENGTH: 27
<212> TYPE: DNA
<213> ORGANISM: Artificial Sequence
<220> FEATURE:
<223> OTHER INFORMATION: SH3RF2 RING 1,2 SH3 forward primer

<400> SEQUENCE: 23
ttgaattccc gtggtcagtc tgcctgg                                       27

<210> SEQ ID NO 24
<211> LENGTH: 26
<212> TYPE: DNA
<213> ORGANISM: Artificial Sequence
<220> FEATURE:
<223> OTHER INFORMATION: SH3RF2 RING 1,2 SH3 reverse primer

<400> SEQUENCE: 24
ttgtcgactc atttgctggg aaacac                                        26

<210> SEQ ID NO 25
<211> LENGTH: 32
<212> TYPE: DNA
<213> ORGANISM: Artificial Sequence
<220> FEATURE:
<223> OTHER INFORMATION: SH3RF2 1,2,3 SH3 forward primer for the mutant
      consisting of the RING domain gene amplification

<400> SEQUENCE: 25
ttgaattcaa atggatgatt tgacgttact tg                                 32

<210> SEQ ID NO 26
<211> LENGTH: 22
<212> TYPE: DNA
<213> ORGANISM: Artificial Sequence
<220> FEATURE:
<223> OTHER INFORMATION: SH3RF2 1,2,3 SH3 reverse primer for the mutant
      consisting of the RING domain gene amplification

<400> SEQUENCE: 26
ttgtcgactc agcagcgcct ca                                            22

<210> SEQ ID NO 27
<211> LENGTH: 20
<212> TYPE: DNA
<213> ORGANISM: Artificial Sequence
<220> FEATURE:
<223> OTHER INFORMATION: PAK4 forward primer

<400> SEQUENCE: 27
gagctgctct tcaacgaggt                                               20

<210> SEQ ID NO 28
<211> LENGTH: 20
<212> TYPE: DNA
<213> ORGANISM: Artificial Sequence
<220> FEATURE:
```

```
<223> OTHER INFORMATION: PAK4 reverse primer

<400> SEQUENCE: 28
ctcctcgttc atcctggtgt                                           20
```